United States Patent [19]

Junge et al.

[11] 4,175,123
[45] Nov. 20, 1979

[54] AMINO-SUGAR DERIVATIVES, PROCESS FOR THEIR PREPARATION AND PHARMACEUTICAL COMPOSITION THEREOF

[75] Inventors: Bodo Junge; Hans-Peter Krause; Lutz Müller; Walter Puls, all of Wuppertal; Jürgen Stoltefuss, Haan, all of Fed. Rep. of Germany

[73] Assignee: Bayer Aktiengesellschaft, Leverkusen, Fed. Rep. of Germany

[21] Appl. No.: 861,043

[22] Filed: Dec. 15, 1977

[30] Foreign Application Priority Data

Dec. 23, 1976 [DE] Fed. Rep. of Germany ....... 2658562
Jun. 10, 1977 [DE] Fed. Rep. of Germany ....... 2726207

[51] Int. Cl.$^2$ ...................... A61K 31/73; C07H 5/06
[52] U.S. Cl. ................................... 424/180; 424/181; 536/4; 536/18; 536/120; 536/1
[58] Field of Search .................. 424/180; 536/18, 4, 536/1, 114, 120, 121; 534/4

[56] References Cited

U.S. PATENT DOCUMENTS

| | | | |
|---|---|---|---|
| 3,480,613 | 11/1969 | Walton | 536/120 |
| 3,914,212 | 10/1975 | Baschang et al. | 536/120 |
| 4,016,261 | 4/1977 | Gordon | 536/120 |
| 4,062,950 | 12/1977 | Frommer et al. | 536/17 |
| 4,065,557 | 12/1977 | Frommer et al. | 536/18 |
| 4,076,930 | 2/1978 | Ellingboe et al. | 536/114 |

*Primary Examiner*—Johnnie R. Brown
*Attorney, Agent, or Firm*—Sprung, Felfe, Horn, Lynch & Kramer

[57] ABSTRACT

The present invention provides amino-sugar derivatives of the general formula

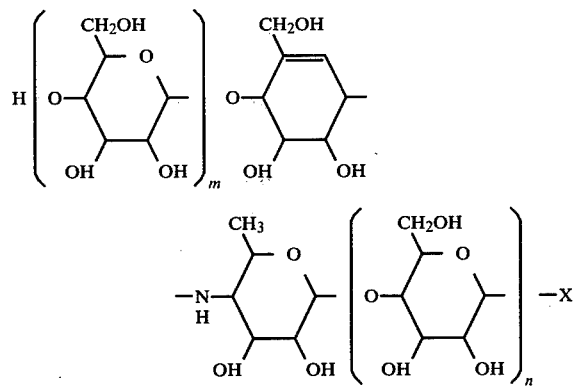

in which n and m independently of each other represent an integer from 0 to 8 and the sum n+m has a value of 0 to 8, and X designates a group —OR, —SH, —SR, —NH$_2$, —NHR or NRR$_1$, in which R designates an alkyl, alkenyl, cycloalkyl, aralkyl, aryl or heterocyclic radical, which can be substituted, and R$_1$ designates an alkyl, cycloalkyl, aralkyl or aryl radical, which can be substituted, or R and R$_1$, together with the nitrogen atom to which they are bonded, form a heterocyclic ring.

It has been found that the compounds of the formula (II) are highly active inhibitors for glycoside hydrolases of the digestive tract.

Also included in the invention are methods of preparing the amino-sugar derivatives of the invention, compositions containing said amino-sugar derivatives and methods for the use of said amino-sugar derivatives and compositions containing them.

10 Claims, No Drawings

AMINO-SUGAR DERIVATIVES, PROCESS FOR THEIR PREPARATION AND PHARMACEUTICAL COMPOSITION THEREOF

The present invention relates to new amino-sugar derivatives, several processes for their preparation and their use as medicaments, in particular as agents against diabetes, adiposity and hyperlipaemia.

A number of Actinomycetes, especially Actinoplanaceae, form oligosaccharise-like inhibitors of α-glucosidases. The higher-molecular compounds ae highly potent inhibitors of α-amylase and the low-molecular compounds are strong saccharase inhibitors with a surprisingly high inhibition of starch digestion in vivo. These inhibitors can be defined by the general formula

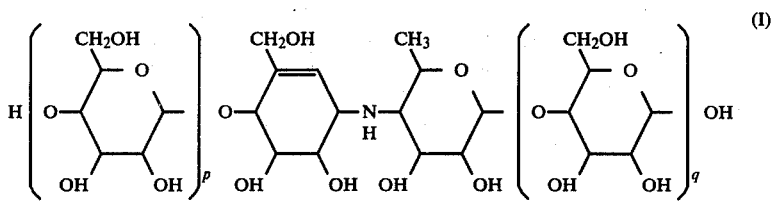

in which

P and q represent an integer from 0 to 8 and the sum of P and q has a value of 1 to 8. (DT-OS (German Published Specification) 2,347,782 and German Patent Application P 2,614,393.1).

The present invention provides amino-sugar derivatives of the general formula

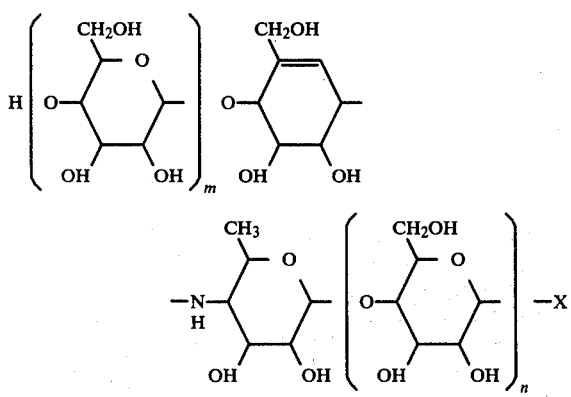

in which n and m independently of each other represent an integer from 0 to 8 and the sum n+m has a value of 0 to 8, and X designates a group —OR, —SH, —SR, —NH$_2$, —NHR or NRR$_1$, in which R designates an alkyl, alkenyl, cycloalkyl, aralkyl, aryl or heterocyclic radical, which can be substituted, and R$_1$ designates an alkyl, cycloalkyl, aralkyl or aryl radical, which can be substituted, or R and R$_1$, together with the nitrogen atom to which they are bonded, form an heterocyclic ring.

It has been found that the compounds of the formula (II) are highly active inhibitors for glycoside hydrolases of the digestive tract.

When R is alkyl, it is preferably straight-chain or branched alkyl with 1 to 30, especially 1 to 18, carbon atoms. Examples which may be mentioned are methyl, ethyl, n-propyl, i-propyl, n-butyl, t-butyl, n-hexyl, n-octyl, octyl-2, dodecyl, lauryl, cetyl and stearyl.

The alkyl radicals R can carry one or more, preferably 1 to 5, identical or different substituents. Examples of substituents which may be mentioned are: hydroxyl, or alkoxy with preferably 1 to 4 carbon atoms, in particular methoxy and ethoxy; amino or monoalkylamino and dialkylamino with preferably 1 to 4 carbon atoms per alkyl radical, in particular monomethylamino, monoethylamino, dimethylamino and diethylamino; mercapto or alkylthio with preferably 1 to 4 carbon atoms, in particular methylthio and ethylthio; halogen, preferably fluorine, chlorine and bromine; alkylcarbonyl with preferably 1 to 4 carbon atoms in the alkyl radical; and carboxyl, nitro, cyano, the aldehyde group and the sulphonic acid group.

It should be mentioned that the radicals derived from sugar derivatives, such as polyalcohols or sugar acids, are of particular interest, in the scope of the present Application, for R in the meaning of a substituted alkyl radical.

When R is alkenyl, it is preferably straight-chain or branched alkenyl with 2 to 6 carbon atoms, which can carry substituents, such as hydroxyl, alkoxy with 1 to 4 carbon atoms, mercapto, alkylthio with 1 to 4 carbon atoms, halogen (preferably fluorine, chlorine and bromine) or nitro.

When R is cycloalkyl it is preferably a carbocyclic radical with 3 to 7 ring carbon atoms (preferably 5 to 7 ring carbon atoms), which can be substituted, possible substituents being the groups and atoms mentioned above in the case of open-chain hydrocarbon radicals R.

When R is aryl it is preferably a monocyclic or bicyclic aromatic radical with 6 to 10 carbon atoms in the aryl part, such as phenyl, biphenyl, naphthyl, etc., in particular phenyl, which can be substituted.

The aryl or aralkyl radicals can carry one or more, preferably 1 to 3, identical or different substituents. Examples of substituents which may be mentioned are: alkyl with 1 to 10 carbon atoms, which in turn can again be substituted, for example by chlorine, nitro or cyano; optionally substituted alkenyl radicals with 1 to 10 carbon atoms; hydroxyl or alkoxy with preferably 1 to 4 carbon atoms; amino or monoalkylamino and dialkylamino with preferably 1 to 4 carbon atoms per alkyl radical; mercapto or alkylthio with preferably 1 to 4 carbon atoms; and carboxyl or carbalkoxy with preferably 1 to 4 carbon atoms; the sulphonic acid group, alkylsulphonyl with preferably 1 to 4 carbon atoms and arylsulphonyl, preferably phenylsulphonyl; aminosulphonyl or alkylaminosulphonyl and dialkylaminosulphonyl with 1 to 4 carbon atoms per alkyl group, preferably methylaminosulphonyl and dimethylaminosulphonyl; nitro, cyano or the aldehyde group; alkylcarbonylamino with preferably 1 to 4 carbon atoms: and alkylcarbonyl with 1 to 4 carbon atoms, benzoyl, benzylcarbonyl and phenylethylcarbonyl, it being possible for the last-mentioned alkyl, phenyl, benzyl and phenylethyl radicals in turn to be again substituted, for example by chlorine, nitro or hydroxyl, as well as radicals derived from sugars.

When R is aralkyl it preferably has 6 to 10, especially 6, carbon atoms in the aryl part said aryl part being preferably monocyclic or bicyclic carbocyclic aryl, such as phenyl, biphenyl or naphthyl, and preferably 1 to 4, especially 1 or 2, carbon atoms in the alkyl part, as for example in benzyl or phenylethyl. Possible substituents for the aryl part of the aralkyl radical are preferably those substituents mentioned for the aryl radicals R above.

When R is a heterocyclic radical, it preferably has a hetero-paraffinic, hetero-aromatic or hetero-olefinic 5-membered or 6-membered ring with preferably 1 to 3 identical or different hetero-atoms. Hetero-atoms are oxygen, sulphur or nitrogen. These ring systems can carry further substituents, for example hydroxyl, amino or $C_1$–$C_4$-alkyl groups, or benzene nuclei or further, preferably 6-membered, heterocyclic rings of the type mentioned can be fused to them.

In this case, the bonding of the heterocyclic radical R is effected via a carbon atom of the heterocyclic system or of the fused benzene nucleus. Particularly preferred heterocyclic radicals are derived, for example, from furane, pyrane, pyrrolidine, piperidine, pyrazole, imidazole, pyrimidine, pyridazine, pyrazine, triazine, pyrrole, pyridine, benzimidazole, quinoline, isoquinoline or purine. Heterocyclic radicals are also to be understood as including those which are bonded via a —$CH_2$— bridge outside the ring, for example the furfuryl radical.

$R_1$ preferably represents a straight-chain or branched alkyl radical with 1 to 6 carbon atoms or a cycloalkyl, aralkyl or aryl radical as defined above for R, such as a cyclopentyl, a cyclohexyl, a benzyl or phenyl radical, it being possible for the radicals mentioned to be preferably substituted by alkoxy with 1 to 4 carbon atoms, amino, $C_1$–$C_4$ monoalkylamino and $C_1$–$C_4$-dialkylamino, nitro, halogen, cyano, hydroxyl, mercapto, $C_1$–$C_4$-thioalkyl or the carboxyl or sulphonic acid group and, in the case where $R_1$ denotes phenyl, also by $C_1$–$C_4$-alkyl.

As indicated above, it is also possible for R and $R_1$, together and including the nitrogen atom to which they are bonded, to form a heterocyclic ring.

This ring can be saturated or unsaturated and can contain 1 to 3 further (preferably 1) oxygen atoms, sulphur atoms or nitrogen atoms and, as hetero groups, a $SO_2$ group or a N-alkyl group, the alkyl in the N-alkyl group preferably containing 1 to 4, in particular 1 or 2, carbon atoms. Methyl, ethyl, n- and i-propyl and n-, i- and t-butyl may be mentioned as alkyl. The heterocyclic ring contains 5 to 7, preferably 5 or 6, ring members. The 6-mentioned heterocyclic ring preferably contains the hetero-atom or the hetero-group in the para-position relative to the nitrogen atom. Examples of the heterocyclic ring which may be mentioned are pyrrolidine, piperidine, piperazine, hexamethyleneimine, morpholine and n-methylpiperazine.

Particularly valuable inhibitors of this invention are those in which n is 1 to 2; amongst these the amino-sugar derivatives of the formulae (III), (IV), and (V) are particularly important.

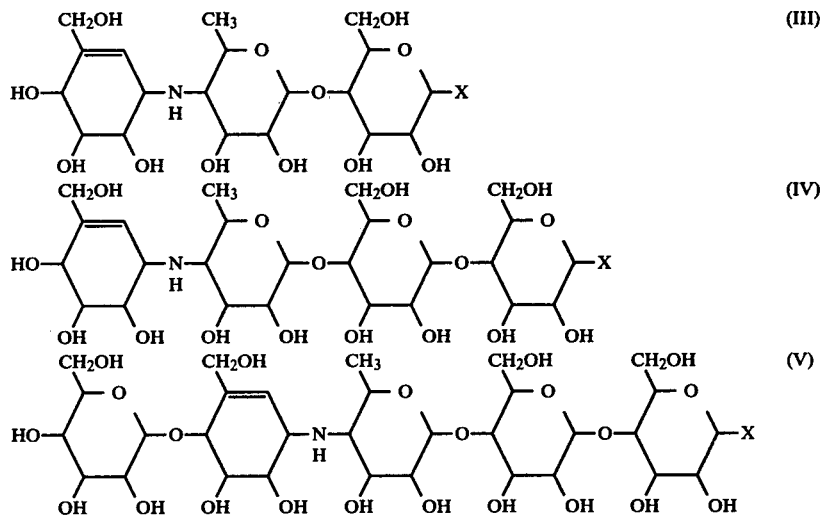

X has the following particularly preferred meanings:
X denotes a —OR, —SH, —SR, —$NH_2$, —NHR or —$NRR_1$ group, in which
R designates an alkyl radical with 1 to 18 carbon atoms, which can be substituted by, to 5 hydroxyl or $C_1$–$C_4$-alkoxy groups; a phenyl radical which is optionally substituted by 1 to 3 $C_1$–$C_4$-alkyl, OH, $C_1$–$C_4$-alkoxy, amino, $C_1$–$C_4$-alkylamino, $C_1$–$C_4$-dialkylamino, carboxyl, methoxycarbonyl, nitro, glucopyranyl, benzoyl, p-hydroxyphenylethylcarbonyl, $C_1$–$C_4$-alkylaminosulphonyl or $C_1$–$C_4$-dialkylaminosulphonyl radicals or by one radical

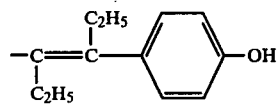

or a benzyl radical or 2-benzthiazolyl radical; and
$R_1$ designates $C_1$–$C_4$-alkyl or, together with R, forms a morpholine or piperidine ring.

Surprisingly, the compounds according to the invention exhibit a higher inhibiting action for α-glucosidases than the non-derivated parent substances and are thus an enrichment of the total range of available medicaments.

Furthermore, the invention provides a process for the preparation of a compound according to the invention of formula (II) in which (1) an acyl halogen derivative of the formula

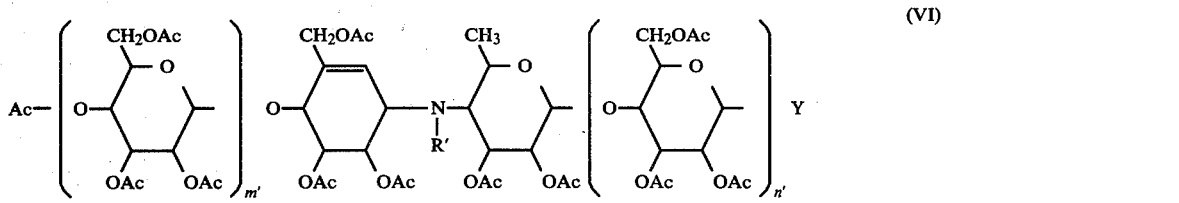

in which m' and n' independently of each other represent a number from 0 to 8 and the sum n'+m' has values of 0 to 8,

in which

R" represents an optionally substituted alkyl, alkenyl cycloalkyl, aralkyl or aryl radical as defined above for R and R' designates hydrogen or the radical Ac defined as above and Y represents halogen (preferably chlorine or bromine), is reacted with a compound of the formula

H—X          (VII)

in which

X has the meaning indicated above, (or a salt thereof in which H is replaced by a metal, such as an alkali or alkaline earth metal, preferably Na or K) optionally in the presence of an acid-binding agent;

(in this process variant an O-acyl halogen compound, that is to say a derivative of the formula (VI) in which R' is hydrogen and a derivative in which R" is a $C_1$-$C_6$- acyl radical or an aroyl radical, preferably acetyl, is preferably employed);

or (2) an ortho-ester of the formula (VIII) (obtainable from the acyl halogen compounds (VI) by reaction with alcohols of the formula $HOR_2$, in which $R_2$ designates alkyl with 1 to 6 carbon atoms or phenyl, preferably methyl or t-butyl)

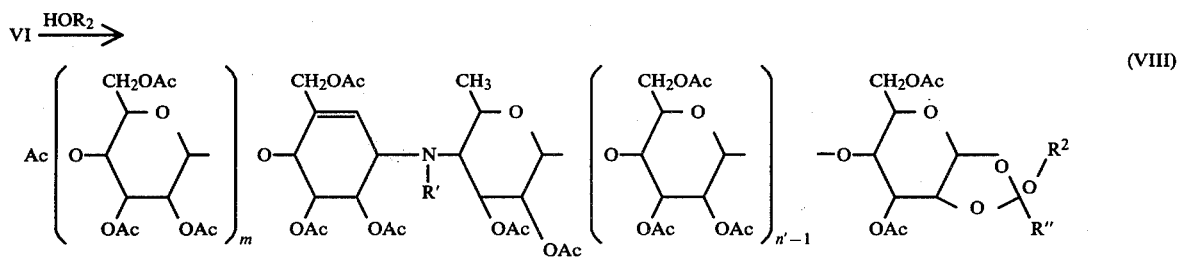

in which

Ac, m', n', $R_2$ and R" have the meanings indicated above, is reacted with a compound of the formula (VII) (for example by the method of Kochetkov [R. L. Whistler and J. N. BeMiller, Methods of Carbohydrate Chemistry, volume VI, page 480, Academic Press, New York and London]);

or (3) a compound of the formula (IX), (obtainable from the acyl halogen compounds (VI) by reaction with $H_2O$, $H_2S$, $NH_3$ or $NH_2R_1$, $R_1$ having the meaning indicated above)

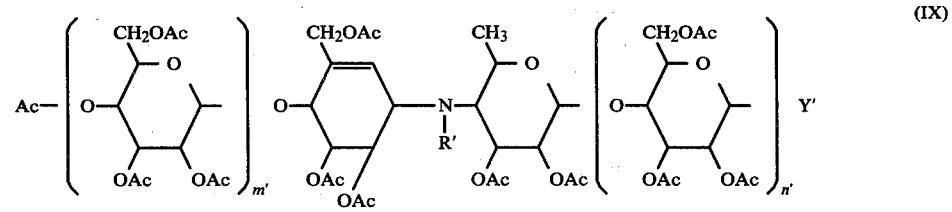

in which m', n', Ac and R' have the meanings indicated above and

Y' is —OH, —SH, —$NH_2$ or $NHR_1$, with the meaning for $R_1$ indicated above, is reacted with a compound of the formula

Z—$R_3$          (X)

in which $R_3$ has the meaning of R indicated above or denotes aryl-N=N— and

Z designates an acid radical, preferably radical of a strong acid, such as —Cl, —Br, —I, —$HSO_4$ or $SO_3H$; (this process variant is particularly suitable for the preparation of the thioethers);

(Note: the esters or amides, which may be obtained in process variants 1-3, of the compounds of the formula (IV) may then be converted into the compounds (VI) by known processes, for example with catalytic amounts of sodium in methanol [G. Zemplen, Ber. 56, 1705 (1923)] or by saponification with aqueous alkali metal hydroxide solutions);

or (4) an acyl derivative, preferably an O-acyl derivative of the formula

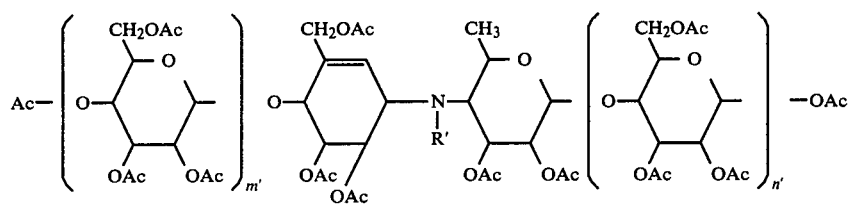

in which m', n', Ac and R' have the meanings indicated above, is reacted with a compound of the formula (VII) (the radicals

or (5) a parent substance of the formula (I) is reacted with a compound of the formula (VII), with the elimination of water, optionally under acid catalysis.

The preparation of the starting compounds of the formula (I) in which P=0 and q=1-7 is known [DT-OS (German Published Specification) 2,347,782].

The starting compounds of the formula (I) in which P and q represent an integer from 0-8 and the sum of n+m can assume a value of 1 to 8, are the subject of German Patent Application P 2,614,393.1. The compounds thus mentioned may be prepared by culturing strains of microorganisms of the order Actinomycetales, in particular of the family Actinoplanaceae, in a manner which is in itself known and by subsequently separating off and isolating the individual compounds, also in a manner which is in itself known.

The compounds of the formula II used as starting materials have not yet hitherto been disclosed, but can be prepared by processes which are customary in sugar chemistry. For example, in order to prepare compounds of the formula (VI) with Y=Br, Ac=acetyl and R'=H, the O-acetyl compounds of the formula (XI) are reacted with HBr in glacial acetic acid at temperatures between −10° C. and room temperature, preferably at 0° C. The reaction time is 15 minutes to 4 hours, preferably about 1 hour. The reaction products are isolated by diluting the reaction mixture with chloroform, removing the acetic acid by washing with water, drying the chloroform phase and evaporating the solution to dryness under reduced pressure in a rotary evaporator. The resulting crude product, that is to say the acetobromo compound, can be used without further purification for the reactions mentioned.

The compounds of the formula (XI) are obtainable from compounds of the formula (I) by processes which are in themselves known, for example by reaction with carboxylic acid chlorides or carboxylic acid anhydrides. In the case of O-acetylation, reaction with acetic anhydride/pyridine for 12 to 48 hours at room temperature has proved suitable.

The compound of the formula (XI) in which m'=0 and n'=0 and R' denotes hydrogen or Ac and Ac represents the acetyl radical is obtainable, for example, by acetolysis of the amino-sugar derivative of the formula (XII)

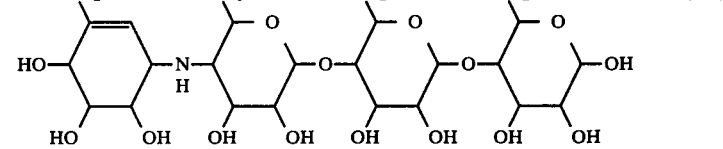

In this procedure, the amino-sugar derivative (XII) is heated with acetic anhydride/glacial acetic acid (1:1) in the presence of catalytic amounts of sulphuric acid, whereupon degradation of the two glucose units and simultaneous acylation of the sugar derivative which remains occurs.

The ortho-esters of the formula (VIII) are also new. However, they can be easily prepared from the compounds of the formula (VI) and alcohols of the formula ($R_2$OH). The alcohols $R_2$OH are preferably employed in excess. The reaction can be carried out with and without diluents; nitromethane is preferably used as a diluent. 2,6-Lutidine is preferably used as an acid-binding agent. The reaction is preferably carried out at room temperature and under normal pressure.

The compounds of the formula (IX) in which Y' designates the mercapto group can be obtained by a process which is in itself known [M. Cerny, D. Zorchystalova and J. Pacak, Collection Czechoslov. Chem. Communs 26, 2206 (1961)] from the acetobromo compounds of the formula (VI) by reaction with thiourea in acetone and subsequent hydrolysis of the reaction products in a weakly alkaline medium (NaHCO$_3$/NaHSO$_3$ in H$_2$O/CHCl$_3$).

The alcohols, polyalcohols, sugar derivatives, phenols, mercaptans, thiophenols and amines of the general formula (VII) are already known. Some compounds of the formula (IV) are mentioned in detail in the following as examples.

It should be expressly emphasised that in the case of the compounds mentioned, polyfunctional compounds can optionally also be employed in the reaction in the form of suitable partially protected derivatives. The protective groups must be appropriately chosen here so that they can be removed again from the reaction product without the glucosidic bonds or the double bond being thereby attacked.

Examples which may be mentioned of compounds of the formula VII are: methanol, ethanol, propanol, isopropanol, tert.-butanol, n-butanol, allyl alcohol, cyclopentanol, n-hexanol, n-octyl alcohol, octanol-2, lauryl alcohol, cetyl alcohol, 1-dimethylamino-propanol-2, benzyl alcohol, furfuryl alcohol, trichloroethanol, ethylene glycol, ethylene glycol monomethyl ether, butane-1,4-diol, D-glucose, D-sorbitol, mesoinositol, pehnol, p-nitrophenol, m-chlorophenol, 2,4-dichlorophenol, 6-chloro-3-hydroxy-toluene, 4-hydroxy-1-tert.butylbenzene, 3-hydroxybenzoic acid, 4-hydroxybenzoic acid, salicylic acid, resorcinol, hydroquinone, phloroglucinol, p-acetamidophenol, diethylstilbestrol, phloretin, phlorhizin, 8-hydroxyquinoline, methylmercaptan, ethylmercaptan, n-propylmercaptan, isopropylmercaptan, n-hexylmercaptan, cyclohexylmercaptan, benzylmercaptan, 1,3-dimercaptopropane, thiophenol, m-thiocresol, p-bromothiophenol, β-thionaphthol, thiohydroquinone, methylamine, dimethylamine, ethylamine, propylamine, dipropylamine, isopropylamine, tert.-butylamine, N-ethyl-N-propylamine, n-hexylamine, dodecylamine, stearylamine, allylamine, ethylenediamine, putrescine, 3-amino-1-dimethylaminopropane, 2-aminoethanol, 2-methylaminoethanol, bis-(2-hydroxy-ethyl)-amine, ethyl 3-amino-propyl ether, 4-amino-2-butanol, cyclohexylamine, benzylamine, pyrrolidine, piperidine, morpholine, piperazine, aniline, N-methylaniline, p-toluidine, o-chloroaniline, m-anisidine, p-nitraniline, m-aminophenol, 4-chloro-3-nitroaniline, p-phenylenediamine, 3-trifluoromethylaniline, α-naphthylamine, benzidine, furfurylamine, 3-aminosulpholane, benzimidazole, hypoxanthine, adenine, uracil, cytosine and 2-desoxystreptamine.

The reaction of compounds of the formula VI with compounds of the formula VII can be carried out with and without a diluent. It is preferably carried out under the conditions of a Königs-Knorr reaction or of one of its more recent variants. Diluents which can be used are all the inert solvents, such as benzene, chloroform, ether or nitromethane, or also basic solvents, such as pyridine or quinoline. The reaction is optionally carried out in the presence of acid-binding agents, Lewis acids and drying agents. Silver salts or mercury salts and drierite are preferably used.

The reaction is generally carried out at temperatures between 0° C. and 100° C., preferably at room temperature, and preferably under normal pressure.

Equimolar amounts of the compounds VI and VII and of the silver salts or mercury salts can be employed in the reaction; however, a large excess of the compounds VII is appropriately also favourable for the reaction. The reaction can also be carried out using metal salts of the compounds VII, for example the alkali metal salts of VII. Silylated derivatives of the compounds VII can also optionally be used.

However, the reaction can also optionally be carried out in protic solvents, such as alcohols, water or a water/acetone mixture. This variant is particularly suitable when the compounds of the formula VII are phenols. In this case, alkali metal hydroxides or alkali metal carbonates are preferably used as acid-binding agents.

If the preparation of the compounds of the formula II is carried out according to the 2nd process, when $R_2$ is methyl, nitromethane is preferably used as the solvent and mercury-II bromide is preferably used as the catalyst in the reaction of the ortho-esters VIII with compounds of the formula VII. If $R_2$ is tert.-butyl, chlorobenzene is preferably used as the solvent and 2,6-lutidinium perchlorate is preferably used as the catalyst. The reaction is preferably carried out under normal pressure and at the boiling point, and a shift of the equilibrium in the direction of the desired reaction product is effected by distilling off volatile reaction products.

If the compounds of the formula II are prepared according to the variant (3) via the intermediate products IX, the reaction of the compounds IX with compounds of the formula X can be carried out, for example, in the following solvents: acetone, dimethylformamide, dioxane, tetrahydrofurane, alcohol, water, chloroform, benzene, acetic acid or mixtures of these solvents. Alkali metal carbonates or alkali metal hydroxides are preferably used as acid-binding agents in this reaction. The reaction can be carried out with equimolar amounts of the compounds X, but also optionally with an excess of X. The reaction is carried out at temperatures between about 0° and 140° C., preferably between about 20° C. and 80° C., and preferably under normal pressure.

The reaction of compounds of the formula XI with compounds of the formula VII can be carried out with and without a diluent. A preferred variant of this process is the reaction of XI with phenol of the formula VII, optionally with an excess of the phenol, in the melt. The reaction is catalysed by protons or Lewis acids. Preferred catalysts are p-toluenesulphonic acid or $ZnCl_2$. The reaction is carried out at temperatures between about 60° and 200° C., preferably between about 80° and 140° C.

The reaction of amines of the formula VII, preferably of aromatic amines, with compounds of the formula XI is preferably carried out using lower alcohols as solvents with the addition of acetic acid, optionally also with an excess of the amine.

The reaction is carried out at temperatures between about 20° and 80° C., preferably at room temperature, and preferably under normal pressure.

The reaction of compounds of the formula I with compounds of the formula VII can be carried out with and without diluents. A preferred variant of this process is the reaction of the compounds I with an excess of lower, anhydrous alcohols of the formula VII, catalysed by mineral acid or cation exchangers.

The reaction is preferably carried out at the boiling point of the alcohol, but can also optionally be carried out at a lower temperature.

If the compounds of the formula VII are amines, preferably aromatic amines, the reaction with compounds of the formula I is preferably carried out by heating the compounds in a little water, as a solvent, or in 50% strength acetic acid or in alcohols, as a solvent, at pH=about 3–4. The reaction can also be carried out by heating the two components without a diluent. The reaction is carried out at temperatures between about 25° and 200° C., preferably between about 60° and 120° C.

In most of the processes, the compounds of the formula II are first obtained as O-acyl derivatives. The splitting off of the acyl protective group is preferably carried out by transesterification under basic catalysis, for example with catalytic amounts of Na in methanol or with triethylamine in methanol, by saponification with alkali metal hydroxides in alcohol/water or by reaction with amines, for example with ammonia in methanol.

The individual procedures for the preparation of the new amino-sugar derivatives are illustrated in the following.

If n-butanol and the compound of the formula VI in which Y is Br, m' is 0, n' is 2, Ac is acetyl and R' is H, are used as the starting materials, the course of the reaction according to variant (1) can be formulated as follows [modified Koenigs-Knorr synthesis according to R. H. Whistler and J. N. BeMiller, Methods in Carbohydrate Chemistry, volume VI, page 474, Academic Press, New York and London].

If phenol is the reactant of the formula VII, an embodiment of variant (1), in which the reaction is carried out with AgO and Drierite as auxiliaries and quinoline as the solvent, or an embodiment in which acetone/H₂O is used as the reaction medium and KOH is used as the acid-binding agent, is preferred.

If 1,2-, 5,6-di-O-isopropylidene-α-D-glucopyranose is used as the alcohol component of the formula VII and the procedure followed is according to process variant (2), the reaction is formulated, for example, as follows [Kochetkov-method according to R. L. Whistler and J. N. BeMiller, Methods in Carbohydrate Chemistry, volume VI, page 480, Academic Press, New York and

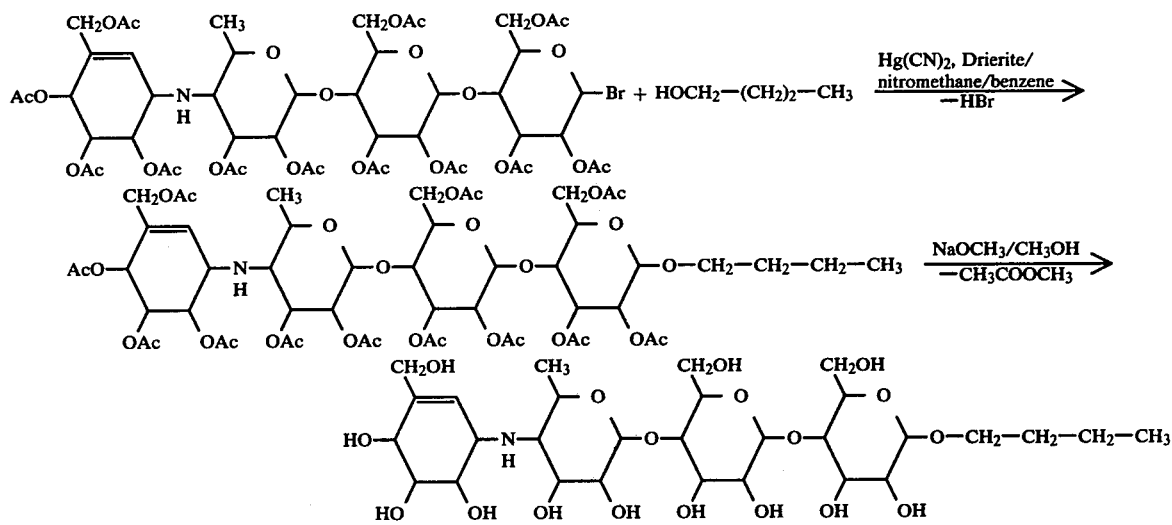

London].

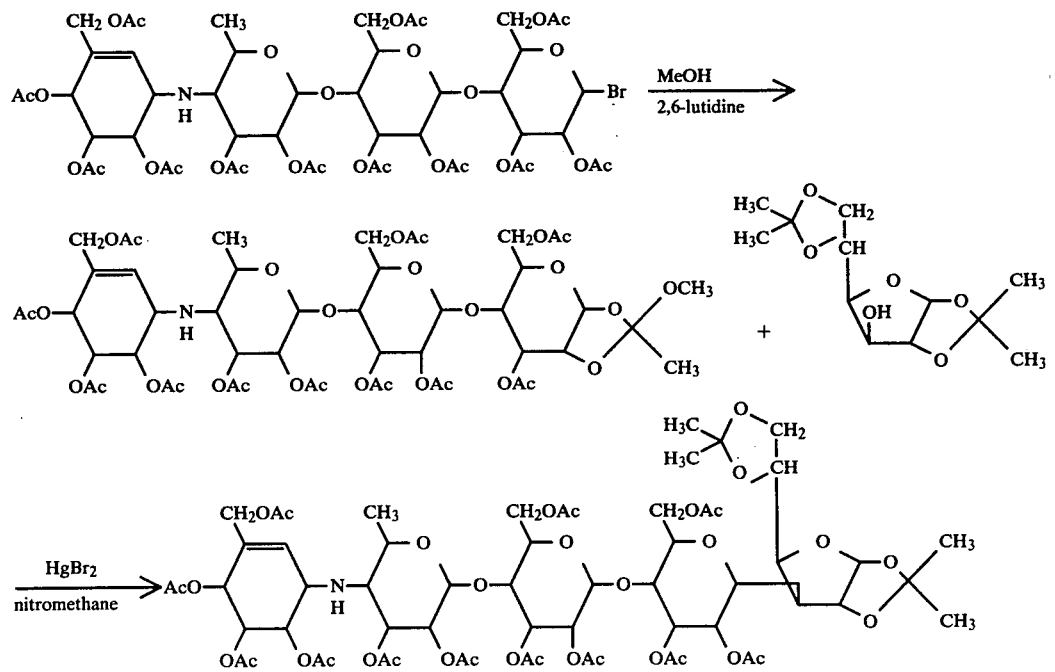

-continued

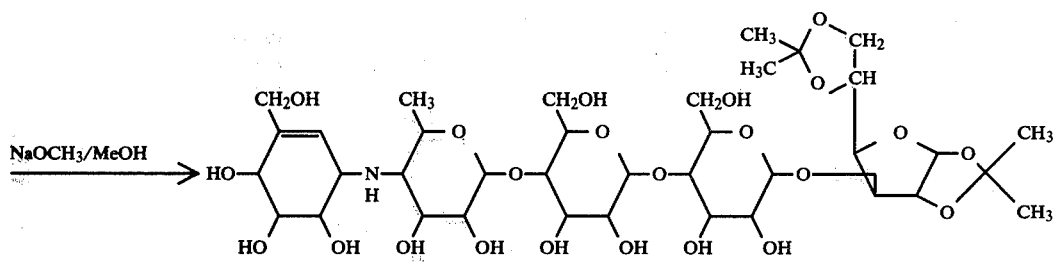

The preparation of a compound of the formula (II) in which -X is for example

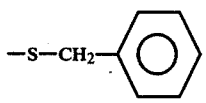

from a compound of the formula (VI) in which, for example, Y is Br, m' is 0, n' is 2, Ac is acetyl and R' is H according to process variant (3), can be described by the following equation [Cerny method according to M. Cerny and J. Pacak, Collection Czechoslov. Chem Communs 24, 2566 (1959) and M. Cerny, J. Vrkoe and H. Stanek, ibid. 24, 64 (1959)].

For the preparation of compounds of the formula (II) in which X is aryl, for example

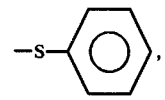

process variant (3) can be modified to the effect that in the third reaction stage the S—H compound is reacted with an aryldiazonium salt, for example with phenyldiazonium chloride, the O-acylated derivative of the formula (II) being formed with the splitting off of HCl and evolution of $N_2$. [Cerny method according to M. Cerny, D. Zachystalova and J. Pacak, Collection Czechosolv. Chem. Communs 26, 2206, (1961)].

If O-acyl derivatives of the formula XI, for example the compound with m'=0, n'=2, Ac=acetyl and R'=H, and p-toluidine are employed as starting materials in the reaction for the preparation of compounds of the formula (II), the course of the reaction can be described as follows:

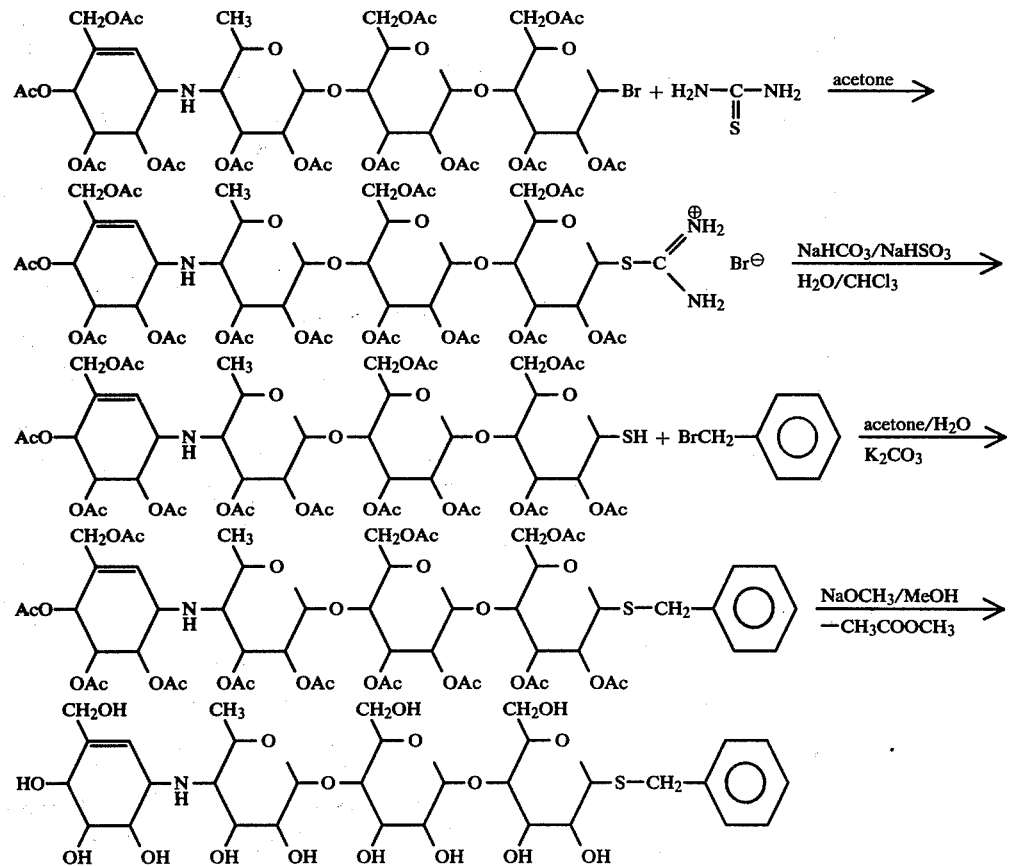

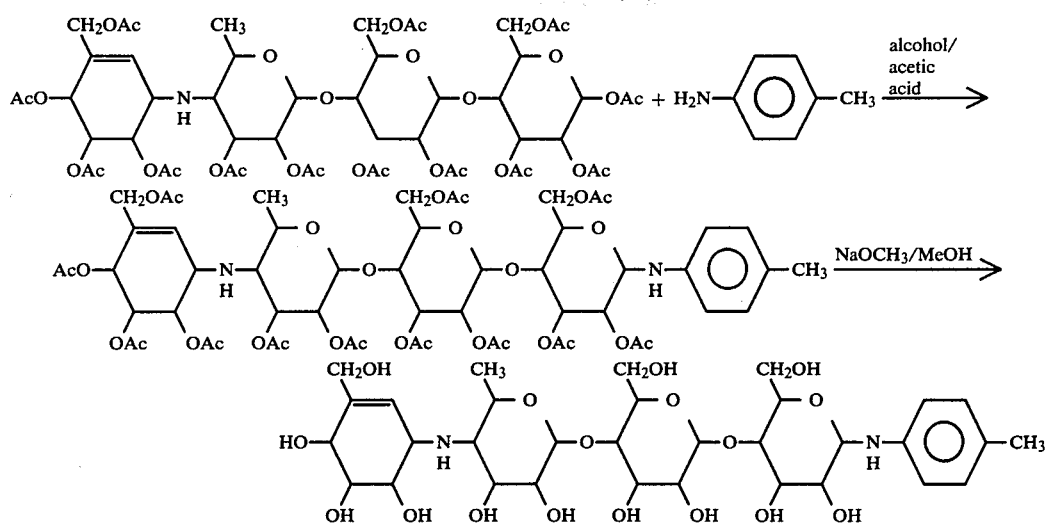

If phenol is the starting material of the formula (VII), the following embodiment of the reaction is preferred [Helferich method according to B. Helferich and E. Schmitz-Hillebrecht, Ber. 66, 378 (1933)].

-continued $$CH_3OH \xrightarrow[-H_2O]{H^\oplus}$$

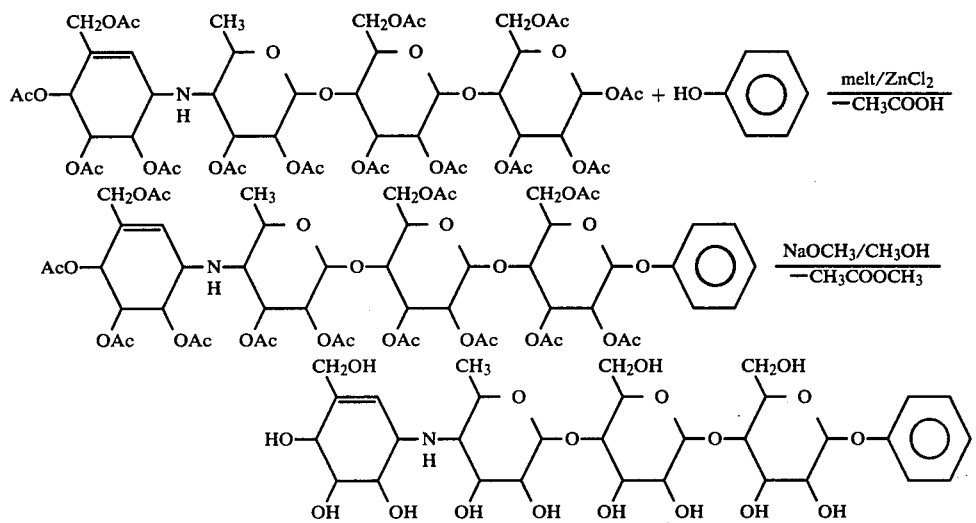

If the compounds of the formula (I) described in DT-OS (German Published Specification) 2,347,782, for example the compound in which m is 0 and n is 1, and, for example, MeOH are employed as starting materials in the reaction for the preparation of compounds of the formula (II), the following equation results [Fischer method according to E. Fischer, Ber. 28, 1151 (1895)].

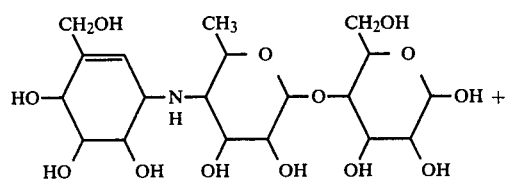

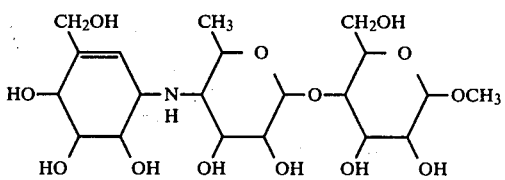

If the compound in which m is 1 and n is 2 is chosen as the starting material of the formula I and p-toluidine is chosen as the starting material of the formula VII, the following equation results:

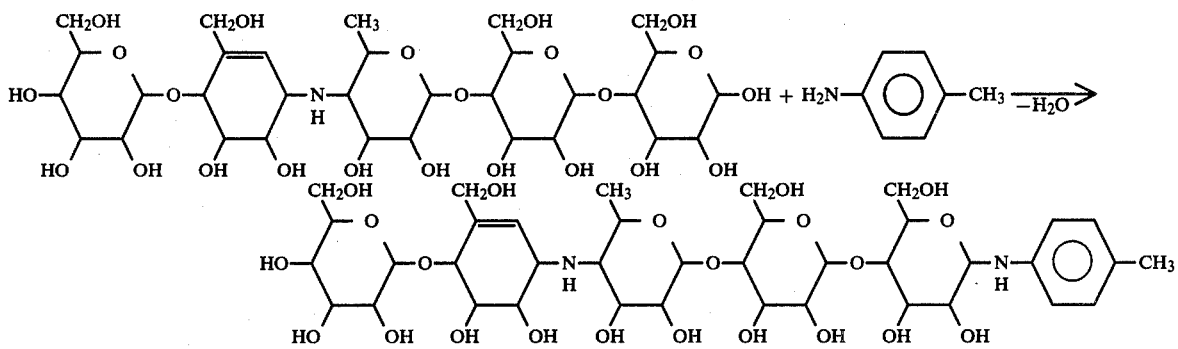

The reaction is carried out between 0° C. and 100° C., preferably at room temperature, and under normal pressure.

The crude active compounds of the formula II are appropriately purified by column chromatography. Chromatography on cellulose, using a butanol/ethanol/water mixture as the running agent, is preferred.

In detail, new active compounds which may be mentioned are the following: {C≡4,6-dideoxy-4-[1S-(1,4,6/5)-4,5,6-trihydroxy-3-hydroxy-methylcyclohex-2-en-1-ylamino]-α-D-glucopyranosyl} phenyl-4,6-didoexy-4-[1S-(1,4,6/5)-4,5,6-trihydroxy-3-hydroxymethylcyclohex-2-en-1-ylamino]-β-D-glucopyranoside, phenyl-4,6-dideoxy-4-[1S-(1,4,6/5)-4,5,6-trihydroxy-3-hydroxymethylcyclohex-2-en-1-ylamino]-β-D-thioglucopyranoside, methyl-4,6-dideoxy-4-[1S-(1,4,6/5)-4,5,6-trihydroxy-3-hydroxymethylcyclohex-2-en-1-ylamino]-α-D-glucopyranoside. Ethyl-O-{C}-(1→4)-β-D-glucopyranoside, methyl-O-{C}-(1→4)-α-D-glucopyranoside, benzyl-O-{C}-(1→4)-β-D-glucopyranoside, phenyl-O-{C}-(1→4)-β-D-glucopyranoside, p-nitrophenyl-O-{C}-(1→4)-β-D-thioglucopyranoside, N-p-tolyl-O-{C}-(1→4)-D-glucopyranosylamine, phenyl-O-{C}-(1→4)-O-α-D-glcp-(1→4)-β-D-glucopyranoside, p-carbomethoxyphenyl-O-{C}-(1→4)-O-α-D-glcop-(1→4)-β-D-glucopyranoside, p-carboxyphenyl-O-{C}-(1→4)-O-α-D-glcp-(1→4)-β-D-glucopyranoside, m-carbomethoxyphenyl-O-{C}-(1→4)O-α-D-glcp-(1→4)-β-D-glucopyranoside, m-carboxyphenyl-O-{C}-(1→4)-O-α-D-glcp-(1→4)-β-D-glucopyranoside, p-hydroxyphenyl-O-{C}-(1→4)-O-α-D-glcp-(1→4)-β-D-glucopyranoside, m-hydroxyphenyl-O-{C}-(1→4)-O-α-D-glcp-(1→4)-β-D-glucopyranoside, p-nitrophenol-O-{C}-(1→4)-O-α-D-glcp-(1→4)-β-D-glucopyranoside, p-tert.-butylphenyl-O-{C}-(1→4)-O-α-D-glcp-(1→4)-β-D-glucopyranoside, methyl-O-{C}-(1→4)-O-α-D-glcp-(1→4)-β-D-glucopyranoside, ethyl-O-{C}-(1→4)-O-α-D-glcp-(1→4)-α-D-glucopyranoside, n-butyl-O-{C}-(1→4)-O-α-D-glcp-(1→4)-β-D-glucopyranoside, benzyl-O-{C}-(1→4)-O-α-D-glcp-(1→4)-β-D-glucopyranoside, n-octyl-O-{C}-(1→4)-O-α-D-glcp-(1→4)-β-D-glucopyranoside, n-hexadecyl-O-{C}-(1→4)-O-α-D-glcp-(1→4)-β-D-glucopyranoside, m-dimethylaminophenyl-O-{C}-(1→4)-O-α-D-glcp-(1→4)-β-D-glucopyranoside, p-dimethylaminosulphonylphenyl-O-{C}-(1→4)-O-α-D-glcp-(1→4)-β-D-glucopyranoside, p-benzoylphenyl-O-{C}-(1→4)-O-α-D-glcp-(1→4)-β-D-glucopyranoside, phenyl-O-{C}-(1→4)-O-α-D-glcp-(1→4)-β-D-thioglucopyranoside, o-aminophenyl-O-{C}-(1→4)-O-α-D-glcp-(1→4)-β-D-thioglucopyranoside, benzyl-O-{C}-(1→4)-O-α-D-glcp-(1→4)-β-D-thioglucopyranoside, n-butyl-O-{C}-(1→4)-O-α-D-glcp-(1→4)-β-D-thioglucopyranoside, carboxymethyl-O-{C}-(1→4)-O-α-D-glcp-(1→4)-β-D-thioglucopyranoside, N-phenyl-O-{C}-(1→4)-O-α-D-glcp-(1→4)-D-glucopyranosylamine, N-p-tolyl-O-{C}-(1→4)-O-α-D-glcp-(1→4)-D-glucopyranosylamine, N-methyl-N-phenyl-O-{C}-(1→4)-O-α-D-glcp-(1→4)-D-glucopyranosylamine, N-p-hydroxyphenyl-O-{C}-(1→4)-O-α-D-glcp-(1→4)-D-glucopyranosylamine, N-propyl-O-{C}-(1→4)-O-α-D-glcp-(1→4)-D-glucopyranosylamine, O-{C}-(1→4)-O-α-D-glcp-(1→4)-D-glucopyranosylmorpholine, O-{C}-(1→4)-O-α-D-glcp-(1→4)-D-glucopyranosylpiperidine, p-aminophenyl-O-{C}-(1→4)-O-α-D-glcp-(1→4)-β-D-glucopyranoside, m-aminophenyl-O-{C}-(1→4)-O-α-D-glcp-(1→4)-β-D-glucopyranoside, naringenindihydrochalcone-4'-[O-{C}-(1→4)-O-α-D-glcp-(1→4)-β-D-glucopyranoside], naringenindihydrochalcone-2'-β-D-glucopyranoside-4'-[O-{C}-(1→4)-O-α-D-glcp-(1→4)-β-D-glucopyranoside], diethylstilbestrol-4'-[O-{C}-(1→4)-O-α-D-glcp-(1→4)-β-D-glucopyranoside], D-sorbitol-4-[O-{C}-(1→4)-α-D-glucopyranoside], O-{C}-(1→4)-O-β-D-glcp-(1→6)-D-glucopyranose, O-{C}-(1→4)-O-α-D-glcp-(1→4)-O-β-D-glcp-(1→6)-D-glucopyranose, p-nitrophenol-O-{4,6-dideoxy-4-[1S-(1,4,6/5)-4,5,6-trihydroxy-3-hydroxymethyl-4-O-α-D-glucopyranosyl-(1→4)-cyclohex-2-en-1-ylamino]-α-D-glucopyranosyl}-(1→4)-O-α-D-glcp-(1→4)-β-D-glucopyranoside, phenyl-O-{4,6-dideoxy-4-[1S-(1,4,6/5)-4,5,6-trihydroxy-3-hydroxymethyl-4-O-α-glucopyranosyl-(1→4)-cyclohex-2-en-1-ylamino]-α-D-glucopyranosyl}-(1→4)-O-α-D-glcp-(1→4)-β-D-thioglucopyranoside, N-p-tolyl-O-{4,6-dideoxy-4-[1S-(1,4,6/5)-4,5,6-trihydroxy-3-hydroxymethyl-4-O-α-D-glucopyranosyl-(1→4)-cyclohex-2-en-1-ylamino]-α-D-glucopyranosyl}-(1→4)-O-α-D-glcp-(1→4)-D-glucopyranosylamine, p-nitrophenyl-O-{C}-(1→4)-O-α-D-glcp-(1→4)-O-α-D-glcp-(1→4)-β-D-glucopyranoside, phenyl-O-{C}-(1→4)-O-α-D-glcp-(1→4)-O-α-D-glcp-(1→4)-β-D-thioglucopyranoside, p-nitrophenyl-O-{4,6-dideoxy-4-[1S-(1,4,6/5)-4,5,6-trihydroxy-3-hydroxymethyl-4-(O-α-D-glcp-(1→4)-O-α-D-glucopyranosyl)-(1→4)-cyclohex-2-en-1-ylamino]-α-D-glucopyranosyl}-(1→4)-O-α-D-glcp-(1→4)-β-D-glucopyranoside, p-nitrophenyl-O-{4,6-dideoxy-4-[1S-(1,4,6/5)-4,5,6-trihydroxy-3-hydroxymethyl-4-(O-α-D-glcp-(1→4)-O-α-D-glcp-(1→4)-O-α-D-glucopyranosyl)-(1→4)-cyclohex-2-en-1ylamino]-α-D-glucopyranosyl}-(1→4)-O-α-D-glcp-(1→4)-β-D-glucopyranoside, O-{C}-(1→4)-O-α-D-glcp-(1→4)-D-glucopyranosylamine and O-{C}-(1→4)-O-α-D-glcp-(1→4)-1-thio-D-glucopyranose.

The compounds according to the invention are inhibitors of glucoside hydrolases and are thus suitable for the treatment of diseases in which an inhibition of these enzymes appears desirable.

It is known that in warm-blooded and cold-blooded animals, after intake of carbohydrate-containing foodstuffs and beverages (for example cereal starch, potato starch, fruit, fruit juice, beer and chocolate), hyperglycaemias arise which are brought about as a result of a rapid degradation of the carbohydrates by glucoside hydrolases (for example salivary and pancreatic amylases, maltases and saccharases) according to the following equation.

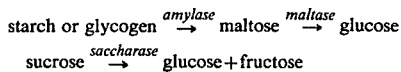

$$\text{starch or glycogen} \xrightarrow{amylase} \text{maltose} \xrightarrow{maltase} \text{glucose}$$

$$\text{sucrose} \xrightarrow{saccharase} \text{glucose} + \text{fructose}$$

In the case of diabetics, these hyperglycaemias are particularly strong and of long-lasting pronounced character. In the case of adipose subjects, the alimentary hyperglycaemia frequently leads to a particularly intense insulin secretion which in turn leads to increased fat synthesis and decreased fat degradation. Following such hyperglycaemias, a hypoglycaemia frequently occurs in the case of adipose persons of sound metabolism, as a result of the insulin secretion. It is known that both hypoglycaemias and foodstuff sludge remaining in the stomach promote the production of gastric juice which in turn causes, or favours, the formation of a gastritis or a gastric or duodenal ulcer.

It is also known that carbohydrates, particularly sucrose, are split in the oral cavity by micro-organisms and the formation of caries is thereby promoted.

Malabsorption of carbohydrates, for example as a result of intestinal saccharase deficiency, causes diarrhoea. Suitable doses of a glucosidase inhibitor effect a synthetic malabsorption and are thus suitable for counteracting constipation.

The inhibitors according to the invention are thus suitable for use as therapeutic agents for the following indications: adiposity, hyperlipoproteinaemia, atherosclerosis, diabetes, pre-diabetes, hypoglycaemia gastritis, constipation and caries.

In order to broaden the spectrum of activity, it can be advisable to combine inhibitors for glucoside hydrolases which complement one another in their action, the combinations being either combinations of the inhibitors according to the invention with one another or combinations of the inhibitors according to the invention with inhibitors which are already known.

In some cases, combinations of the inhibitors according to the invention with known oral antidiabetic agents ($\beta$-cytotropic sulphonylurea derivatives and/or biguanides having an action on the blood sugar) and with blood lipid-lowering active compounds, such as, for example, clofibrate, nicotinic acid, cholestyramine and others, are also advantageous.

The compounds can be administered without dilution, for example as a powder or in a gelatine casing, or in combination with an excipient in a pharmaceutical composition.

The present invention provides a pharmaceutical composition containing as active ingredient a compound of the invention in admixture with a solid or liqufied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possible over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent. The envelope is coloured.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded or cold-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously) or rectally. Preferred pharmaceutical compositions and medicaments are therefore those adapted for such administration.

In general it has proved advantageous to administer amounts of 30 to $30 \times 10^5$ AIU/kg and of 1 to $1 \times 10^4$ SIU/kg of body weight per day to achieve effective results. Nevertheless it can at times be necessary to deviate from those dosage rates, and in particular to do so as a function of the nature and body weight of the animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

In addition to the abovementioned pharmaceutical compositions, foodstuffs containing these active compound can also be prepared; for example sugar, bread, potato products, fruit juice, beer, chocolate and other confectionery, and preserves, such as, for example, jam, a therapeutically active amount of at least one of the inhibitors according to the invention having been added to these products.

Furthermore, the inhibitors according to the invention have the property, in animals, of influencing, to a high degree, the ratio of the proportion of undesired fat to the proportion of desired meat of low fat content (lean meat) in favor of the lean meat. This is of particular importance for the rearing and keeping of agricultural stock animals, for example in the enhancing the anabolic growth of pigs, but is also of considerable importance for the rearing and keeping of other stock animals and pets. Furthermore, the use of the inhibitors can lead to a considerable rationalisation of the feeding of the animals, both in respect of time, quantity and quality. Since they cause a certain delay in digestion, the residence time of the nutrients in the digestive tract is extended, whereby ad libitum feeding associated with less expense is made possible. Furthermore, in many cases a considerable saving of valuable protein feed results when the inhibitors according to the invention are used.

The active compounds can thus be used in virtually all sections of animal nutrition as agents for reducing the formation of fatty layers and for the saving of feed protein.

The activity of the active compounds here is largely independent of the nature and the sex of the animals. The active compounds prove particularly valuable in species of animals which generally tend to deposit relatively large amounts of fat or tend to do so during certain stages of their life.

The following stock animals and pets may be mentioned as examples of animals with which the inhibitors for reducing the formation of fatty layers and/or for saving feed protein can be employed: warm-blooded animals, such as cattle, pigs, horses, sheep, goats, cats, dogs, rabbits, fur-bearing animals, for example mink and chinchillas, and other pets, for example guinea pigs and hamsters, laboratory animals and zoo animals, for example rats, mice, monkeys and the like, poultry, for example chickens, geese, ducks, turkeys and pigeons, parrots and canaries, and cold-blooded animals, such as fish, for example carp, and reptiles, for example snakes.

Because of the favourable properties of the active compounds, the amount of active compounds administered to the animals in order to achieve the desired effect can be substantially varied. It is preferably about 0.5 mg to 2.5 g/kg, in particular 10 to 100 mg/kg, of feed. The period over which the active compound is administered can be from a few hours or days to several years. The appropriate amount of active compound and the appropriate period over which it is administered are closely connected with the object of feeding. In particular, they depend on the nature, the age, the sex and the state of health of the animals and on the method of keeping the animals and can be easily determined by any person skilled in the art.

The active compounds according to the invention are administered to the animals by the customary methods. The nature of the administration depends, in particular, on the nature, the behaviour and the general condition of the animals. Thus, it is possible to carry out the administration orally once or several times daily, at regular or irregular intervals. In most cases, oral administration, in particular in the rhythm of the food and/or drink intake of the animals, is to be preferred for reasons of expediency.

The active compounds can be administered as pure substances or in the formulated form, the formulated form being understood both as a premix, that is to say mixed with non-toxic inert excipients of any desired nature, and also as part of a total ration in the form of a supplementary feed and as a constituent of the mixture of a mixed feed by itself. Aministration of suitable formulations by means of the drinking water is also included.

The active compounds, optionally in the formulated form, can also be administered together with other nutrients and active compounds, for example mineral salts, trace elements, vitamins, proteins, energy carriers (for example starch, sugar or fats), dyestuffs and/or flavouring substances or other feedstuff additives, such as, for example, growth promoters, in a suitable form. The active compounds can be administered to the animals before, during or after the food intake.

Oral administration together with the feed and/or drinking water is advisable, the active compound being added to the total amount or only to parts of the feed and/or drinking water, depending on the requirement.

The active compounds can be added to the feed and/or the drinking water according to the customary methods by simple mixing as the pure substances, preferably in the finely divided form, or in the formulated form mixed with edible, non-toxic excipients, and optionally also in the form of a premix or a feed concentrate.

The feed and/or drinking water can, for example, contain the active compounds according to the invention in a concentration from about 0.001 to 5.0%, in particular about 0.02 to 2.0% (weight). The optimum level of the concentration of the active compound in the feed and/or drinking water depends, in particular, on the amount of feed and/or drinking water intake of the animals and can be easily determined by any expert.

The nature of the feed and its composition is not important here. It is possible to use all the usual commercially available or special feed compositions, which preferably contain the customary balance of energy substances and proteins, including vitamins and mineral substances, necessary for balanced nutrition. The feed can be composed, for example, of vegetable substances, for example shredded oilcake, shredded cereal and cereal by-products, but also of hay, silage fodder, beets, and other forage plants, of animal substances, for example meat and fish products, bonemeal, fats and vitamins, for example A, D, E, K and B-complex, as well as special sources of protein, for example yeasts and certain aminoacids, and mineral substances and trace elements, such as, for example, phosphorus and iron, zinc, manganese, copper, cobalt, iodine and the like.

Premixes can preferably contain about 0.1 to 50%, in particular about 0.5 to 5.0%, (weight) of the active compounds of the formula II, in addition to any desired edible excipients and/or mineral salts, for example carbonated feed lime, and are prepared by the customary mixing methods.

Mixed feeds preferably contain about 0.001 to 5.0%, in particular about 0.02 to 2.0%, (weight) of the active compounds of the formula II, in addition to the customary raw material components of a mixed feed, for example shredded cereal or cereal by-products, shredded oilcake, animal protein, minerals, trace elements and vitamins. They can be prepared by the customary mixing methods.

The active compounds in premixes and mixed feed agents can preferably also be appropriately protected from air, light and/or moisture by suitable agents which cover their surface, for example with non-toxic waxes or gelatine.

The following is an example of the composition of a finished mixed feed, for poultry, containing an active compound according to the invention: 200 g of wheat, 340 g of maize, 360.3 g of coarse soya bean meal, 60 g of beef tallow, 15 g of dicalcium phosphate, 10 g of calcium carbonate, 4 g of iodinated sodium chloride, 7.5 g of a vitamin/mineral mixture and 3.2 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_4.H_2O$, 140 mg of $ZnSO_4.7H_2O$, 100 mg of $FeSO_4.7H_2O$ and 20 mg of $CuSO_4.5H_2O$.

The active compound premix contains, for example, the active compound from Example 1, 8 in the desired amount, for example 1,600 mg, and in addition 1 g of DL-methionine and enough soya bean flour to form 3.2 g of premix.

The following is an example of the composition of a mixed feed, for pigs, which contains an active compound of the formula II: 630 g of shredded cereal feed (composed of 200 g of shredded maize, 150 g of shredded barley, 150 g of shredded oats and 130 g of shredded wheat), 80 g of fishmeal, 60 g of coarse soya bean meal, 58.8 g of tapioca flour, 38 g of brewer's yeast, 50 g of a vitamin/mineral mixture for pigs (composition, for example, as in the chicken feed), 30 g of linseed cake meal, 30 g of maize gluten feed, 10 g of soya bean oil, 10 g of cane sugar molasses and 2 g of active compound premix (composition, for example, as in the chicken feed) give, after careful mixing, 1 kg of feed.

The feed mixtures indicated are intended, preferably, for rearing and fattening chicken or pigs respectively; however, they can also be used, in an identical or similar composition, for rearing and fattening other animals.

In vitro α-amylase inhibition test

The in vitro α-amylase inhibition test makes it possible to determine the enzyme inhibitory activity of the sample by comparing the activity of commercially obtainable α-amylase from the pig's pancreas in the presence of the inhibitor with its activity in the absence (so-called 100% value) of the inhibitor. For this, soluble starch is used as the substrate; the enzyme activity determination is based on the colorometric determination of reducing groups by means of dinitrosalicylic acid.

An amylase inhibitory unit (AIU) is defined as that inhibitory activity which reduces a given amylolytic activity in a defined test batch by one unit (amylase unit=AU); the amylase unit is defined here as that enzyme activity which in one minute under given conditions splits one μmol of glucosidic bonds and thus leads to the formation of one μmol of reducing groups.

200 μl of solution of α-amylase from the pig's pancreas (crystal suspension "BOEHRINGER") in 20 mM sodium glycerophosphate buffer of pH 6.9, of 1 mM strength in $CaCl_2$ are added to 10 μl of a sample solution which is diluted so that it contains 0.05–0.15 AIU in the said aliquot and the mixture is pre-incubated for 10 minutes at 37° C. The amylase solution is to be adjusted to an activity of 2.0–2.5 AU/ml. The amylolytic reaction is then started by adding 200 μl of a 5% strength solution of starch ("MERCK 1257") in sodium glycerophosphate buffer of pH 6.9, of 1 mM strength in $CaCl_2$ and after an incubation period of 5 minutes at 37° C. is stopped by adding 0.5 ml of dinitrosalicylic acid reagent (S. P. COLOWICK + N. O. KAPLAN, editors: Meth. Enzymol. 1 (1955) 149). In order to develop the colour, the mixture is heated to 100° C. for 5 minutes, after which it is diluted with 2.5 ml of $H_2O$ and measured photometrically at 540 nm against a reagent blank (without enzyme).

In order to calculate the enzyme activities in the presence and in the absence of the inhibitor, standards are set up with 1 and 2 μmols of maltose in 400 μl of sodium glycerophosphate buffer; the extinction for 1 μmol of reducing groups is obtained from the extinction difference between the two standards. This value is used in a known manner in the calculation of the enzyme activities (in amylase units). The specific inhibitory activity of the inhibitor, expressed in amylase inhibitory units per gramm (AIU/g) is obtained from the activity difference between the uninhibited and inhibited batch, taking into account the amounts of inhibitor employed.

In vitro saccharase inhibition test

The in vitro saccharase inhibition test makes it possible to determined the enzyme inhibitory activity of a sample by comparing the activity of the solubilised intestinal disaccharidase complex in the presence of the inhibitor with its activity in the absence (so-called 100% value) of the inhibitor. A virtually glucose-free (<100 ppm) saccharose is used here as the substrate, which determines the specificity of the inhibition test; the enzyme activity determination is based on the colorometric determination of liberated glucose by means of glucoseoxydase, peroxydase and 2,2-azino-di-[3-ethylbenzthiazoline-6-sulphonate] (=ABTS) as the chromogen.

A saccharase inhibitor unit (SIU) is defined as that inhibitory activity which reduces a given saccharolytic activity in a defined test batch by one unit (saccharase unit=SU); the saccharase unit is defined here as that enzyme activity which, under given conditions, in one minute splits 1 μmol of sucrose and thus leads to the liberation of 1 μmol each of glucose, which is determine in the test, and fructose, which is not detected in the test.

The intestinal disaccharidase complex is obtained from pig's small intestine mucosa by trypsin digestion, precipitation from 66% ethanol at −20° C., taking up of the precipitate in 100 mM phosphate buffer of pH 7.0 and concluding dialysis against the same buffer.

100 μl of a dilution of the intestinal disaccharidase complex in 0.1 M maleate buffer of pH 6.25 are added to 10 μl of a sample solution which is diluted so that the extinction of the test batch is at least 10%, but not more than 25%, below that of the 100% value, and the mixture is pre-incubated for 10 minutes at 37° C. The dilution of the disaccharidase complex is to be adjusted to an activity of 0.05 SU/ml. The saccharolytic action is then started by adding 100 μl of a 0.4 M solution of sucrose ("SERVA 35579") in 0.1 M maleate buffer of pH 6.25 and after an incubation period of 20 minutes at 37° C. is stopped by adding 1 ml of GOD/POD/ABTS reagent (50 mg of GOD, degree of purity II, "BOEHRINGER"+30 mg of POD, degree of purity II "BOEHRINGER"+2 g of ABTS, "BOEHRINGER" in 1,000 ml of 0.5 M tris buffer at pH 7.0). In order to develop the colour, the mixture is incubated for 30 minutes at 37° C., after which it is diluted with 2 ml of tris buffer and measured photometrically at 420 nm against a reagent blank (with enzyme but without sucrose).

The calculation of the inhibitory activity of inhibitors is made more difficult by the fact that even slight alterations in the test system, for example a 100% value which varies slightly from determination to determination, have an influence on the test results which can no longer be disregarded. These difficulties are avoided by simultaneously running a standard in each determination; the compound of the formula I (page 2) with m=0 and n=2, which has a specific inhibitory activity of 68,000 SIU/g and, when amounts of 5 and 10 mg are employed, leads to an inhibition in the test of the order of size specified above, is used as the standard. When the difference in the extinctions at 420 nm between the 100% value and the batch inhibited by the standard is known, the specific inhibitory activity of the inhibitor, expressed in saccharase inhibitor units per gram (SIU/g) can be calculated in a known manner from the extinction difference between the 100% value and the batch inhibited by the sample solution, taking into account the amount of inhibitor employed.

In vitro method for the inhibition of glucose absorption

The inhibition of glucose absorption by the compounds according to the invention were demonstrated in a modified experimental arrangement according to Crane and Mandelstam [Biochem. Biophys. Acta 45 (1960) 460–476].

The upper part of the small intestine of fasting male Wistar rats is folded over and cut into rings about 3 mm wide. 10 of these rings (~150 mg moist weight) are incubated for 2 minutes at 37° C. in 5 ml of Krebs-Ringer bicarbonate buffer (pH 7.4) with D-glucose-$^{14}$C (U) (10 mg/ml, 0.2 μCi/ml), with the addition of the active compounds. The washed and dried-off intestine rings are weighted, dissolved in 5 ml of Digestin (Merck)/isopropanol (1:1) and the radioactivity absorbed in the tissue is determined in a liquid scintillation counter. All values are corrected using the radioactivity absorbed in the tissue as D-mannitol-1-$^{14}$C.

Results

In vitro inhibitions of the glucose absorption by some selected compounds (10 mg/ml):

Table I

| Number of the compound in the Preparation Examples | Inhibition(*) |
| --- | --- |
| Example 1, 8 | + |
| Example 1, 7 | + |
| Example 1, 9 | ++ |
| Example 1, 5 | ++ |
| Example 4, 18 | ++ |

(*)Inhibition 25-50% of the control value +
Inhibition > 50% of the control value ++

The in vivo activity of the compound was tested on some examples using the experimental arrangement described in the following text.

Oral administration of starch or sucrose causes a rise in the blood sugar in warm-blooded animals, provided that the carbohydrates are enzymatically degraded in the small intestine to monosaccharides. The inhibition of their enzymatic hydrolysis by glucosidase inhibitors causes a reduced rise in the blood sugar.

In order to detect the action of glucosidase inhibitors, 6 fasting rats receive perorally, 1 g of broiled starch or 2.5 g of sucrose/kg in the form of an aqueous suspension or in the form of an aqueous solution (starch and sucrose control respectively). An equal number of rats receive the glucosidase inhibitor in the dose indicated, together with the same amount of the carbohydrate concerned. An equal volume of physiological sodium chloride solution is administered orally to a further six rats (control). After administration of the carbohydrate concerned ± glucosidae inhibitor, the postprandial change in blood sugar is measured, at the times indicated, in blood from the postorbital venous plexus in an auto-analyser according to the method of W. S. Hoffmann [J biol. Chem 120, 51 (1937)].

It was shown here that the active compounds according to the invention are highly active inhibitors of starch and sucrose digestion and in low doses already have a high activity and long-lasting period of action.

Table II contains the results of the starch feeding test and Table III shows those of the sucrose feeding test.

Table II

| Dose/kg perorally | Blood sugar in mg/dl ± standard deviation | | | |
| --- | --- | --- | --- | --- |
| | 15 | 30 | 45 | 60 minutes |
| Fasting control | 82 ± 12 | 72 ± 10 | 102 ± 6.7 | 88 ± 7.4 |
| Starch control | 146 ± 19 | 144 ± 8.9 | 120 ± 7.9 | 118 ± 6.9 |
| Starch + 10 mg of 2 | 102 ± 10 | 73 ± 9.1 | 100 ± 6.5 | 108 ± 9.3 |
| Starch + 10 mg of 20 | 87 ± 12 | 83 ± 13 | 99 ± 17 | 111 ± 5.6 |
| Starch + 10 mg of 13 | 70 ± 8.3 | 40 ± 6.8 | 89 ± 9.0 | 100 ± 4.6 |
| Fasting control | 60 ± 4.2 | 62 ± 3.4 | | |
| Starch control | 131 ± 7.2 | 113 ± 9.2 | | |
| Starch + 0.78 mg of 6 | 110 ± 6.1 | 105 ± 10 | | |
| Starch + 0.65 mg of 8 | 112 ± 9.9 | 109 ± 12 | | |
| Starch + 0.92 mg of 3 | 89 ± 8.0 | 97 ± 13 | | |
| Starch + 0.86 mg of 1 | 93 ± 6.4 | 84 ± 12 | | |
| Starch + 1.56 mg of 4 | 99 ± 8.1 | 97 ± 10 | | |
| Starch + 0.92 mg of 7 | 121 ± 7.7 | 112 ± 4.3 | | |

— — probability <0.05    ——— probability <0.01    ═══ probability <0.001 compared with the corresponding starch control.

Table III

| Dose/kg perorally | Blood sugar in mg/dl ± standard deviation | | | |
|---|---|---|---|---|
| | 15 | 30 | 45 | 60 minutes |
| Fasting control | 61 ± 13 | 65 ± 3.9 | 66 ± 6.9 | 76 ± 3.7 |
| Sucrose control | 113 ± 6.5 | 116 ± 9.2 | 104 ± 12 | 123 ± 8.1 |
| Sucrose + 10 mg of 2 | 79 ± 4.1 | 86 ± 10 | 74 ± 7.2 | 71 ± 15 |
| Sucrose + 10 mg of 20 | 83 ± 20 | 85 ± 8.3 | 73 ± 8.5 | 69 ± 9.3 |
| Sucrose + 10 mg of 13 | 79 ± 6.8 | 80 ± 5.4 | 85 ± 16 | 86 ± 2.0 |
| Sucrose + 10 mg of 15 | 80 ± 6.1 | 83 ± 9.4 | 87 ± 4.8 | 94 ± 13 |
| Fasting control | 60 ± 4.6 | 64 ± 3.7 | 73 ± 7.1 | 66 ± 4.2 |
| Sucrose control | 128 ± 8.0 | 133 ± 8.7 | 134 ± 6.1 | 119 ± 10 |
| Sucrose + 0.78 mg of 6 | 96 ± 15 | 100 ± 3.4 | 106 ± 18 | 117 ± 6.5 |
| Sucrose + 0.65 mg of 8 | 112 ± 3.1 | 114 ± 6.3 | 119 ± 9.4 | 112 ± 4.3 |
| Sucrose + 0.92 mg of 3 | 97 ± 10 | 108 ± 4.2 | 112 ± 15 | 111 ± 11 |
| Sucrose + 0.86 mg of 1 | 103 ± 6.4 | 110 ± 10 | 108 ± 13 | 107 ± 11 |
| Sucrose + 1.56 mg of 4 | 95 ± 7.0 | 112 ± 5.5 | 104 ± 6.7 | 115 ± 7.0 |
| Sucrose + 0.92 mg of 7 | 110 ± 3.4 | 118 ± 14 | 112 ± 10 | 117 ± 9.0 |
| Fasting control | 71 ± 3.7 | 70 ± 5.3 | 77 ± 5.5 | 78 ± 7.3 |
| Sucrose control | 134 ± 13 | 116 ± 20 | 125 ± 8.6 | 112 ± 15 |
| Sucrose + 3.0 mg of 9 | 85 ± 4.8 | 83 ± 7.9 | 88 ± 3.4 | 92 ± 9.4 |
| Sucrose + 1.54 mg of 22 | 80 ± 3.7 | 79 ± 5.2 | 86 ± 4.5 | 86 ± 11 |

– – probability 0.05 —— probability 0.01

= probability 0.001 compared with the corresponding sucrose control

On the preparation of the starting compounds

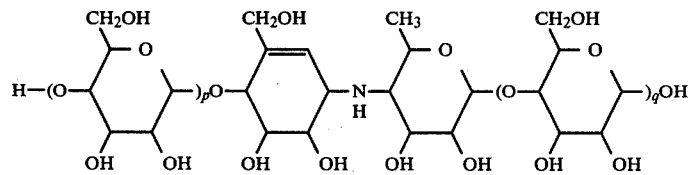

A column with a diameter of 1.5 cm was filled with 30 g (moist weight) of Dowex® 50 W×4, (H+), 200–400 mesh, in 0.001 N HCl. 500 ml of mixed desorbed products (400,000 SIU/l, pH 2.5, 60% acetone), obtained according to Example 10, Table, consecutive No. 7, of DT-OS (German Published Specification) 2,347,782, was then pumped through the column in about 1 hour and the column was then rinsed with 500 ml of 0.001 N HCl. Under these conditions, activity was eluted only in traces. Subsequently, the product was desorbed with 0.0125 N HCl and the conductivity or the refractive index of the column eluate was recorded. In addition, the SIU content of the eluate was tested. The active fractions 74–100 were combined and neutralised by adding Amberlite IRA 410 OH⁻, and then concentrated to 5 ml and digested with 5 ml of methanol and the product was precipitated by adding the mixture dropwise to 200 ml of acetone. After washing with acetone and ether, the product was dried in vacuo.

Yield: 1 g of the compound with P+q=2, containing 65,000 SIU/g.

The compounds with p+q=3 to 8 glucose units are obtained from the runnings and the active preliminary fractions.

In contrast to alkaline desorption, this process of acid desorption thus makes fractionation of the individual amino-sugar derivatives of this series possible.

In order to separate the isomeric compounds with three glucose units, 10 g of an isomer mixture, dissolved in water, were washed with water, on a column filled with Dowex® 50 W×4 (H+), until the eluate was neutral and then eluted with 0.025 N hydrochloric acid. Fractions of 3 ml each were collected and examined by thin layer chromatography. The thin layer chromatography was carried out on silanised silica gel plates (MERCK, Germany) using 100:60:40:2 ethyl acetate+methanol+water+25% strength ammonia, with threefold development. The compound with p=0 and q=3 runs a greater distance from the starting compound than the compound with p=1 and q=2. Fractions 215 to 272, containing 6 g of isomer with p=1 and q=2, and fractions 288 to 294, containing 600 mg of isomer with p=0 and q=3, were combined, neutralised with Amberlite IRA-410 (OH—) and concentrated.

The in vitro sucrose inhibitory activity of the isomers with p=0 and q=3, isolated by this process, is 19,000 SIU/g.

The preparation of further starting compounds is described in Examples 8, 23; 8, 25; 9, 26: 9, 27 and 9, 28.

Preparation Examples for the amino-sugar derivatives according to the invention

EXAMPLE 1 p-Nitrophenyl-O-{C}-(1→4)-O-α-D-glcp-(1→4)-β-D-glucopyranoside (C≡4,6-Dideoxy-4-[1S-(1,4,6/5)-4,5,6-trihydroxy-3-hydroxymethylcyclohex-2-en-1-ylamino]-α-D-glucopyranosyl)

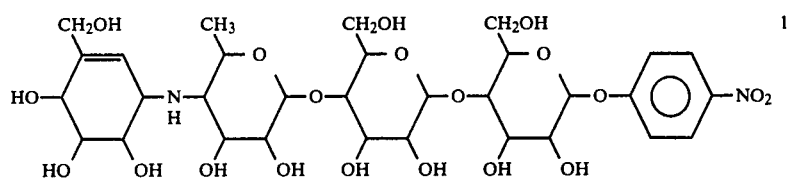

5 g of drierite, 1.2 g (8.6 mmols) of p-nitrophenol and 1 g (4.3 mmols) of silver oxide are added to 40 ml of absolute quinoline and the mixture is stirred for 30 minutes, with the exclusion of moisture. 10 g of compound 26 from Example 9 are then added and the mixture is allowed to come to room temperature slowly, whilst stirring vigorously.

The reaction mixture is stirred for a further 12 hours at room temperature, 300 ml of chloroform are added and the insoluble residue is separated off. The chloroform solution is washed, whilst cooling with ice, first with 5% strength hydrochloric acid, then with sodium carbonate solution and finally with water and is then dried. The residue is added to a solution of 400 mg of sodium in 100 ml of absolute methanol and the mixture is stirred for 2 hours at room temperature. It is then diluted with 100 ml of water and neutralised with a weakly acid ion exchanger (H+ form), the exchanger is separated off and the solution is evaporated to dryness on a rotary evaporator. The residue is taken up in a little dimethylformamide/water and discharged onto a column (length: 70 cm; φ: 2.6 cm) filled with cellulose (Avicel, Merck).

The column is eluted with butanol which is saturated with water and the individual fractions are examined by thin layer chromatography. 3 g of the non-crystalline compound 1 with an optical rotation value $\alpha_D=88.8°$ ($H_2O$; c=1%) are obtained.

For further characterisation, a small amount of the compound is acetylated in acetic anhydride/pyridine at room temperature and a mass spectrum of the resulting dodecaacetate of the compound 1 is recorded.

Molecular weight determined by mass spectrometry: 1,270 ($C_{55}H_{72}N_2O_{32}$).

The following compounds were prepared in an analogous way:

2:
Phenyl-O-{C}-(1→4)-O-α-D-glcp-(1→4)-β-D-glucopyranoside

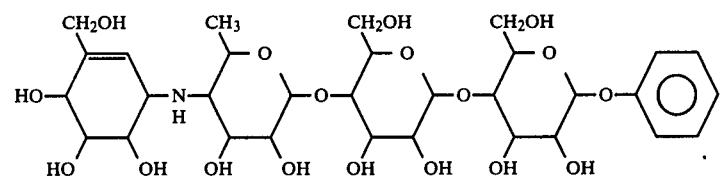

$\alpha_D=101.6°$ ($H_2O$; c=1%)

The mass spectrum of the acetylated compound and the $H^1$—NMR and $C^{13}$—NMR spectra were measured.

3:
m-Hydroxyphenyl-O-{C}-(1→4)-O-α-D-glcp-(1→4)-β-D-glucopyranoside

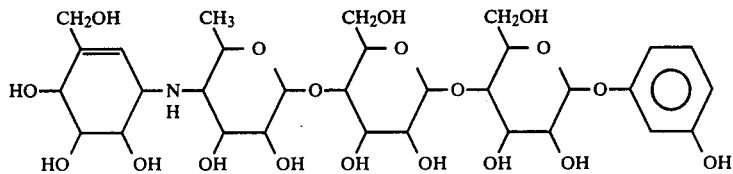

(O-Acetylresorcinol was employed as the starting compound)

$\alpha_D=100.2°$ ($H_2O$; c=1%)

Molecular weight of the acetylated compound, determined by mass spectrometry: 1,283 ($C_{57}H_{73}NO_{32}$)

4:
m-Carbomethoxyphenyl-O-{C}-(1→4)-O-α-D-glcp-(1→4)-β-D-glucopyranoside

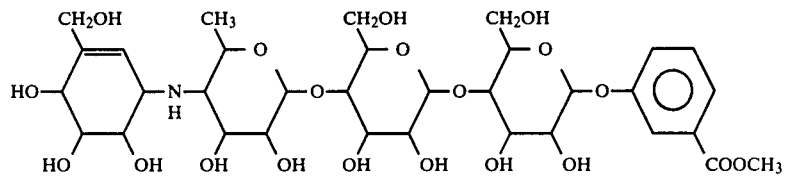

$\alpha_D = 71.0°$ (H$_2$O; c=1%)

Molecular weight of the acetylated compound, determined by mass spectrometry: 1,283 (C$_{57}$H$_{73}$NO$_{32}$)

5:
m-Carboxyphenyl-O-{C}-(1→4)-O-α-D-glcp-(1→4)-β-D-glucopyranoside

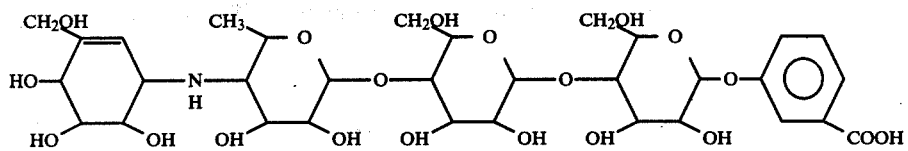

5 was prepared by saponifying 4 with 10% strength sodium hydroxide solution at room temperature.
$\alpha_D = 91.7°$ (H$_2$O; c=1%)

6:
p-Carbomethoxyphenyl-O-{C}-(1→4)-O-α-D-glcp-(1→5)-β-D-glucopyranoside

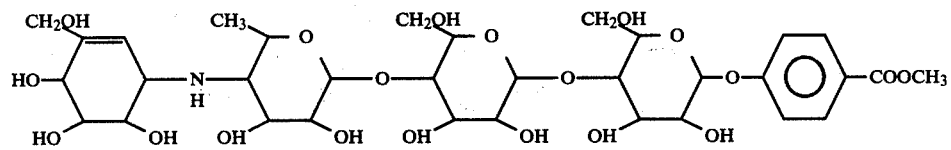

Molecular weight of the acetylated compound, determined by mass spectrometry: 1,283 (C$_{57}$H$_{73}$NO$_{32}$)

7:
p-Carboxyphenyl-O-{C}-(1→4)-O-α-D-glcp-(1→4)-β-D-glucopyranoside

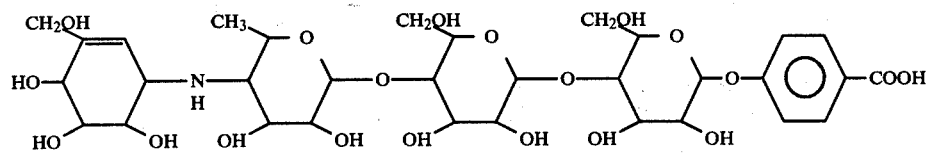

7 was prepared by saponifying 6 with 10% strength sodium hydroxide solution at room temperature.
$\alpha_D = 85.9°$ (H$_2$O; c=1%)

8:
p-Hydroxyphenyl-O-{C}-(1→4)-O-α-D-glcp-(1→4)-β-D-glucopyranoside

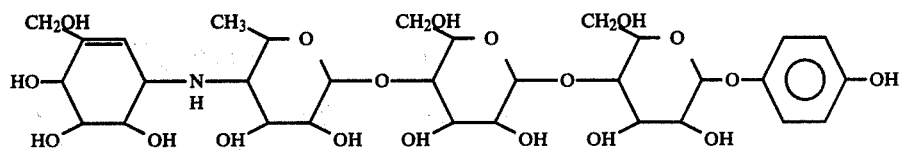

(O-Benzoyl-hydroquinone was employed as the starting compound)

Molecular weight of the acetylated compound, determined by mass spectrometry: 1,283 (C$_{57}$H$_{73}$NO$_{32}$)

9:
p-tert-Butylphenyl-O-{C}-(1→4)-O-α-D-glcp-(1→4)-β-D glucopyranoside

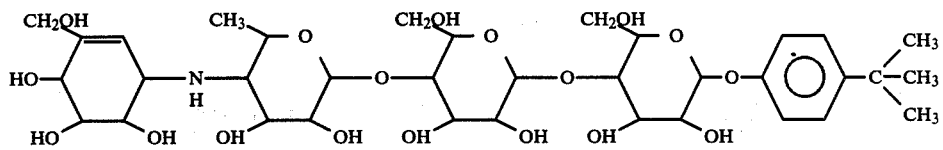

Molecular weight of the acetylated compound, determined by mass spectrometry: 1,281 (C$_{59}$H$_{79}$NO$_{30}$)

10:
Diethylstilbostrol-4'-[O-{C}-(1→4)-O-α-D-glcp-(1→4)-β-D-glucopyranoside]

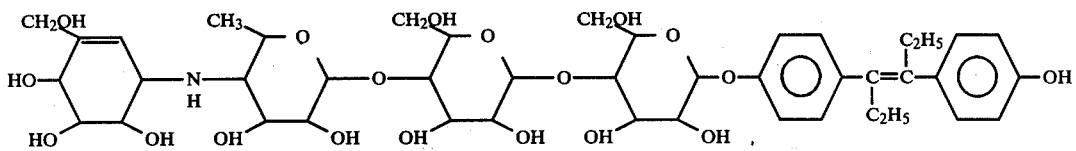

After acetylation, the compound was characterised by mass spectrometry.

11:

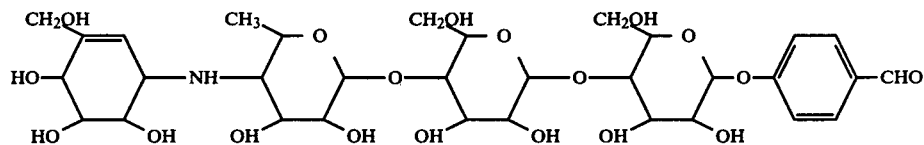

Naringenindihydrochalcone-2'-β-glucopyranoside-4'-[O-{C}-(1→4)-O-α-D-glcp-(1→4)-β-D-glucopyranoside]

13:
4-Formyl-phenyl-O-{C}-(1→4)-O-α-glcp-(1→4)-β-D-glucopyranoside

Molecular weight of the acetylated compound, determine by mass spectrometry: 1,253 ($C_{56}H_{71}NO_{31}$)

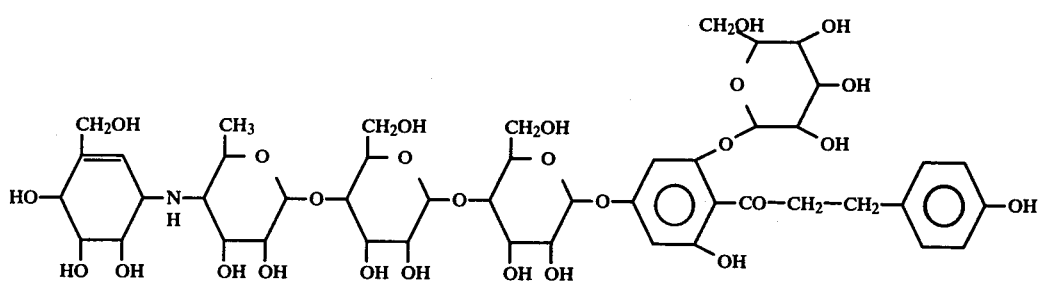

(Phlorhizin was employed as the starting compound)
$C_{46}H_{65}NO_{27}$ (1,064.0)

14:
4-(β-Cyanoethenyl)-phenyl-O-{C}-(1→4)-O-α-D-glcp-(1→4)-β-D-glucopyranoside

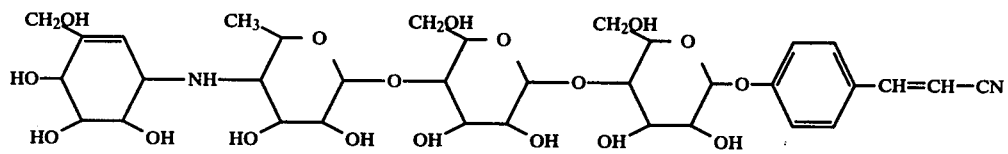

Calculated: C 51.9; H 6.2; N 1.3; O 40.6; Found: C 51.6; H 7.1; N 0.8; O 38.5

Molecular weight of the acetylated compound: 1,276 ($C_{58}H_{72}N_2O_{30}$)

12:
p-Nitrophenyl-O-{4,6-dideoxy-4-[IS-(1,4,6/5)-4,5,6-trihydroxy-3-hydroxymethyl-4-O-α-D-glucopyranosyl-(1→4)-cyclohex-2-en-1-ylamino]-α-D-glucopyranosyl}-(1→4)-O-α-D-glcp-(1→4)-β-D-glucopyranoside 15:
4-Cyclohexyl-phenyl-O-{C}-(1→4)-O-α-D-glcp-(1→4)-β-D-glucopyranoside

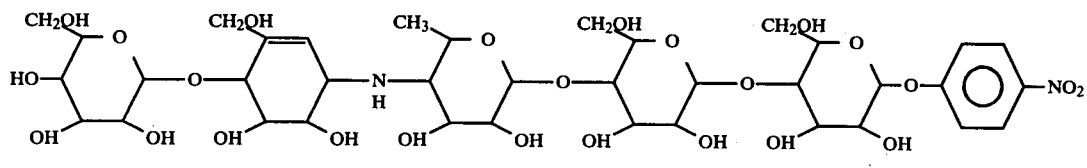

The product was characterised by a $C^{13}$-NMR spectrum and a mass spectrum of the acetylated compound

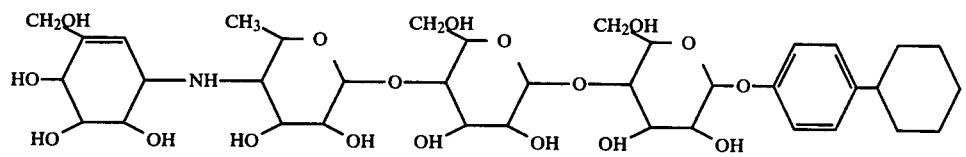

16:
3-(β-Cyanoethenyl)-phenyl-O-{C}-(1→4)-O-α-D-glcp-(1→4)-β-D-glucopyranoside 8.8 g (7.3 mmols) of the compound 26 from Example 9 in 22 ml of acetone were added, at room temperature, to a solution of 3.2 g (34 mmols) of phenol and 1.08 g (19.3 mmols) of KOH in 14 ml of H₂O. The mixture was

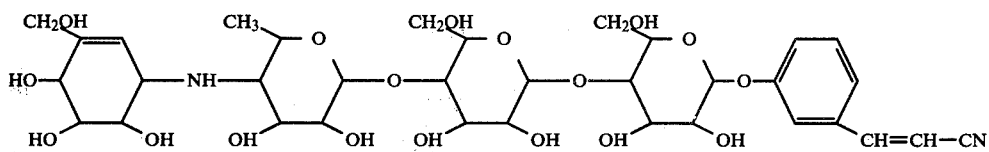

Analogous to Preparation Example 1

3-Dimethylamino-phenyl-O-{C}-(1→4)-O-α-D-glcp-(1→4)-β-D-glucopyranoside stirred overnight and then diluted with 50 ml of benzene. The organic phase was separated off and concentrated in a rotary evaporator. The residue was taken up in 200 ml of benzene and the benzene solution was ex-

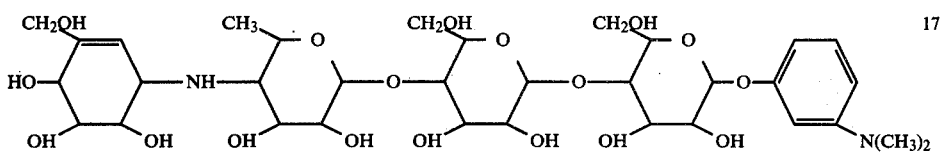

$\alpha_D = 73.22°$ (H₂O; C=1)
Molecular weight of the acetylated compound, determined by mass spectrometry: 1,268 ($C_{37}H_{76}N_2O_{30}$).

4-Dimethylaminosulphonyl-phenyl-O-{C}-(1→4)-O-α-D-glcp-(1→4)-β-D-glucopyranoside tracted by shaking first with 20 ml of water, then with 40 ml of 2 N NaOH and finally 3 times with 80 ml of water each time. The benzene phase was dried, filtered and concentrated. Residue: 6.4 g.

The residue was stirred overnight in a solution of 50

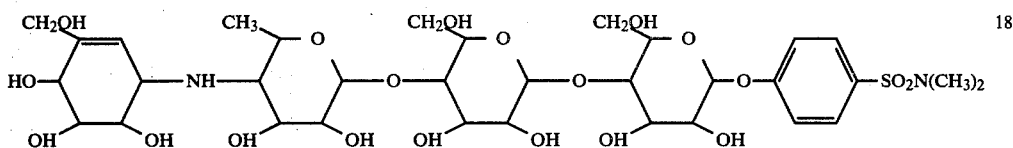

$\alpha_D = 85.4°$ (H₂O; C=1)
Molecular weight of the acetylated compound, determined by mass spectrometry: 1,332 ($C_{57}H_{76}N_2O_{32}S$).

4-Benzoyl-phenyl-O-{C}-(1→4)-O-α-D-glcp-(1→4)-β-D-glucopyranoside mg of Na in 50 ml of MeOH. The mixture was then diluted with water and neutralised with Amberlite IRC 50 (H⁺ form). After filtration, the solution was evaporated to dryness in a rotary evaporator. Residue: 3.2 g.

The residue was discharged onto a column (50 cm long, φ: 2.4 cm) filled with cellulose (Merck: "Avicel").

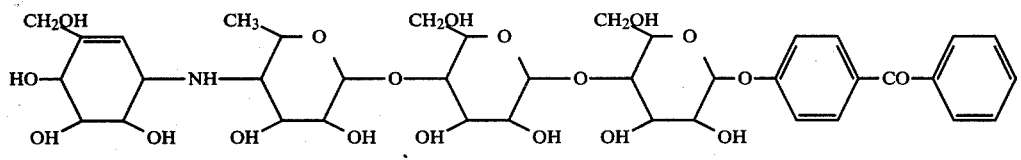

$\alpha_D = 75.46°$ (H₂O; C=1%)
Molecular weight of the acetylated compound, determined by mass spectrometry: 1,329 ($C_{62}H_{75}NO_{31}$).

EXAMPLE 2:

Phenyl-O-{C}-(1→4)-O-α-D-glcp-(1→4)-β-D-glucopyranoside

Butanol saturated with water was used as the eluting agent. The dropping rate was 15 drops/minute; fractions of 400 drops each were collected. Fractions 36–57 gave 1.5 g of non-crystalline 2.

The following compound was prepared in an analogous way:

Phenyl-O-C-(1→4)-β-D-glucopyranoside

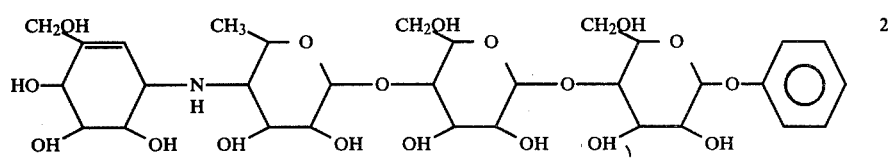

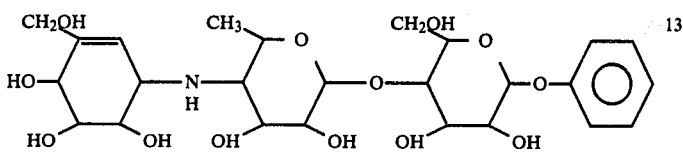

The product was characterised by a proton resonance spectrum at 220 MHz, a $^{13}$C-NMR spectrum and a mass spectrum of the acetylated compound.

EXAMPLE 3:

Methyl-O-{C}-(1→4)-O-α-D-glcp-(1→4)-β-D-glucopyranoside

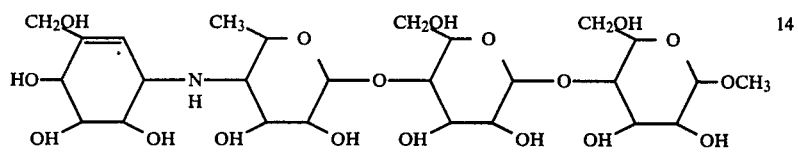

1.3 g of yellow mercury-II oxide, 0.1 g of mercury-II bromide and 2.0 g of drierite are stirred in 20 ml of absolute methanol and 20 ml of pure chloroform for half an hour at room temperature. 3.0 g of the compound 26 from Example 9 are then added and the mixture is stirred overnight. The insoluble residue is filtered off and the filtrate is evaporated to dryness in a rotary evaporator. The residue is taken up in chloroform and the solution is once more clarified by filtration and then concentrated again.

The residue is stirred overnight with 75 ml of a 0.1% strength solution of sodium methanolate in methanol at room temperature. The mixture is then diluted with water to 400 ml and neutralised with a weakly acid ion exchanger (H+ form). The solvent is removed in a rotary evaporator and the residue is discharged onto a column (length: 70 cm; φ: 2.4 cm) filled with cellulose ("Avicel", Merck). The column is eluted with butanol-/ethanol/water 3:1:1.

Fractions of about 8 ml are collected and the individual fractions are examined by thin layer chromatography. Fractions 60-92 contain 500 mg of the compound 14.

After acetylation with acetic anhydride/pyridine, a mass spectrum of the compound was measured. Molecular weight determined by mass spectrometry: 1,163 ($C_5OH_{69}NO_{30}$).

The following compound was prepared in an analogous way:

Ethyl-O-{C}-(1→4)-β-D-glucopyranoside

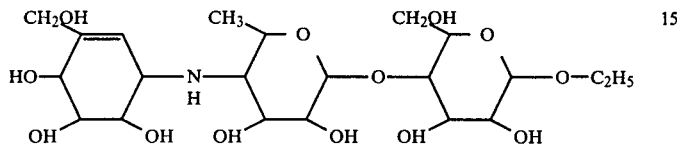

Molecular weight of the acetylated compound, determined by mass spectrometry: 889 ($C_{39}H_{55}NO_{22}$).

EXAMPLE 4:

n-Butyl-O-{C}-(1→4)-O-α-D-glcp-(1→4)-β-D-glucopyranoside

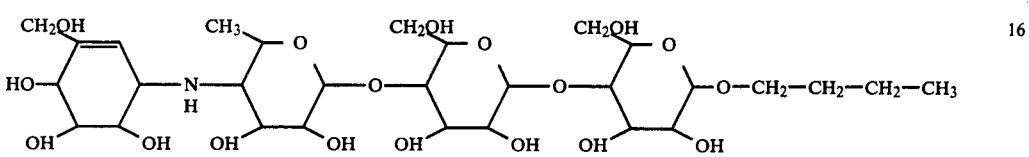

20 ml of liquid are distilled off from a mixture of 40 ml of nitromethane and 40 ml of benzene, with the exclusion of moisture. After cooling, 1 ml of n-butanol and 1 g of drierite are added and the mixture is stirred for 30 minutes at 40° C. 0.5 g of mercury-II cyanide and 2.4 g of the compound 26 from Example 9 are then added and the mixture is warmed to 40° to 50° C. for a further 24 hours. The reaction mixture is then diluted with benzene and the benzene solution is washed first with water, then with a sodium bicarbonate solution and finally with water again.

After drying, the solution is evaporated to dryness on a rotary evaporator. The residue is de-acetylated overnight at room temperature with 50 ml of a 0.1% strength solution of sodium methanolate in methanol. The mixture is diluted with water and neutralised with a weakly acid ion exchanger. The solution is concentrated in a rotary evaporator and the residue is discharged onto a column filled with cellulose. The column is eluted with butanol which is saturated with water. The individual fractions are examined by thin layer chromatography. 500 mg of the non-crystalline compound 16 are obtained. Molecular weight of the acetylated compound, determined by mass spectrometry: 1,205 ($C_{53}H_{75}NO_{30}$).

The following compounds were prepared in an analogous way:

n-Octyl-O-{C}-(1→4)-O-α-D-glcp-(1→4)-β-D-glucopyranoside

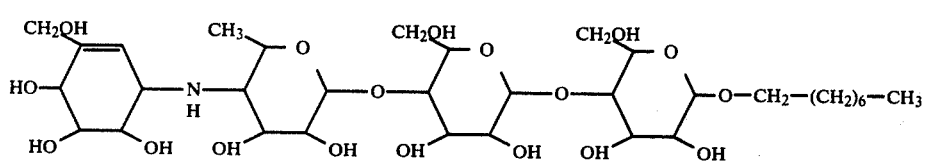

n-Hexadecyl-O-{C}-(1→4)-O-α-D-glcp-(1→4)-β-D-glucopyranoside

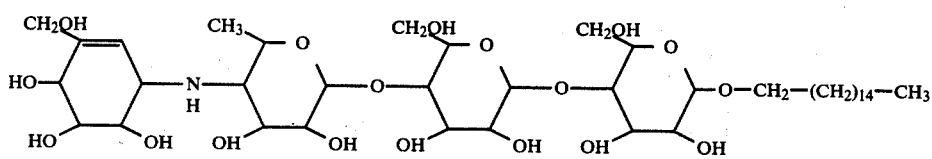

Benzyl-O-{C}-(1→4)-O-α-D-glcp-(1→4)-β-D-glucopyranoside

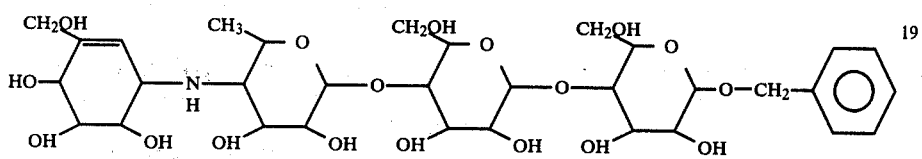

Molecular weight of the acetylated compound, determined by mass spectrometry: 1,239 ($C_{56}H_{73}NO_{30}$).

Benzyl-O-{C}-(1→4)-β-D-glucopyranoside

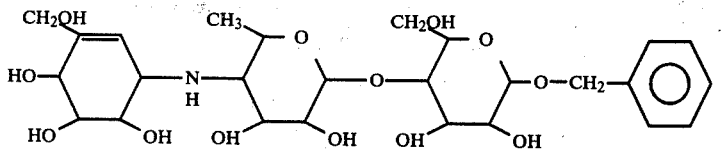

Molecular weight of the acetylated compound, determined by mass spectrometry: 951 ($C_{44}H_{57}NO_{22}$).

EXAMPLE 5:

Methyl-O-{C}-(1→4)-α-D-glucopyranoside

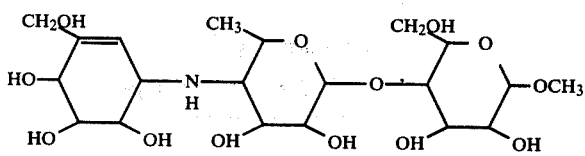

1 g of O-{C}-(1→4)-α-D-glcp-(1→4)-D-glucopyranose was heated under reflux in 100 ml of absolute methanol and 2 ml of concentrated sulphuric acid for 10 hours. After cooling, the mixture was diluted with 100 ml of water and the solution was neutralised with NaCO$_3$. The mixture was filtered and the filtrate was concentrated in a rotary evaporator. The residue was dissolved in a little water and discharged onto a column filled with a strongly acid ion exchanger (Dowex 50 WX4, H+ form). The column was eluted first with water and then with 0.025 N HCl. The individual fractions were investigated by thin layer chromatography. Fractions 44–60 gave 360 mg of 21. Molecular weight of the acetylated compound, determined by mass spectrometry: 875 ($C_{38}H_{53}NO_{22}$).

The α-configuration of the glucoside is demonstrated by a proton resonance spectrum at 100 MHz.

EXAMPLE 6:

Methyl-O-{C}-(1→4)-α-D-glucopyranoside

[structure 20]

1 g of O-{C}-(1→4)-D-glucopyranose was warmed to 60° C. in 100 ml of 1% strength methanolic hydrochloric acid for 24 hours. The solution was then evaporated to dryness on a rotary evaporator.

The residue was taken up in water and the solution was then neutralised with a basic ion exchanger (OH− form). The aqueous solution was discharged onto a column filled with a strongly acid ion exchanger (Dowex 50 WX4, H+ form). The further procedure was as described under Example 5. Yield: 500 mg of 21.

EXAMPLE 7:

D-Sorbitol-4-[O-C-(1→4)-α-D-glucopyranoside]

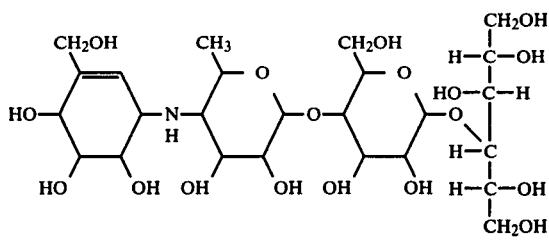

1 g of O-{C}-(1→4)-O-α-D-glcp-(1→4)-D-glucopyranose was dissolved in 50 ml of distilled water. The solution was adjusted to pH 10 with 1% strength sodium hydroxide solution. 100 mg of NaBH$_4$ were then added and the mixture was stirred for 48 hours at room temperature. It was neutralised with a weakly acid ion exchanger and the aqueous solution was discharged onto a column filled with a strongly acid ion exchanger (Dowex WX4, H$^+$ form). The column was eluted first with water and then 0.05 N hydrochloric acid. 370 mg of 22 were obtained.

$\alpha_D = 96.8°$ (H$_2$O; c=1%).

Molecular weight of the acetylated compound, determined by mass spectrometry: 1,235 (C$_{53}$H$_{73}$NO$_{32}$).

EXAMPLE 8:

Trideca-O-acetyl-O-{C}-(1→4)-O-β-D-glcp-(1→4)-D-glucopyranose

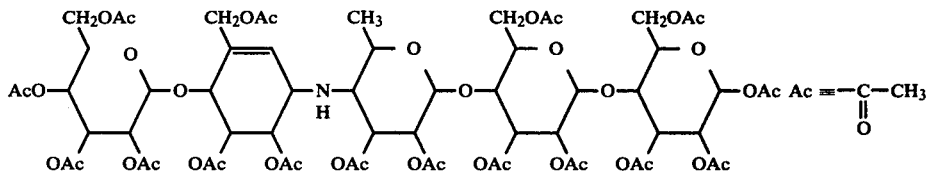

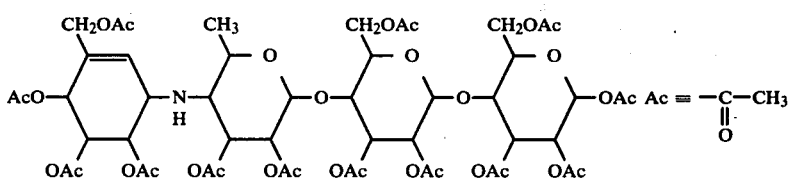

3.8 g of O-{C}-(1→4)-O-α-D-glcp-(1→4)-D-glucopyranose were stirred for 48 hours in 50 ml of acetic anhydride and 50 ml of pyridine at room temperature. The mixture was then concentrated in a rotary evaporator, the residue was taken up in chloroform and the chloroform solution was extracted by shaking three times with water and dried with Na$_2$SO$_4$. After removing the solvent, 6.2 g of non-crystalline 23 were obtained.

The molecular weight of the compound, determined by mass spectrometry, is 1,191 (C$_{51}$H$_{69}$NO$_{31}$).

The following compounds were prepared analogously:

Deca-O-acetyl-O-{C}-(1→4)-D-glucopyranose

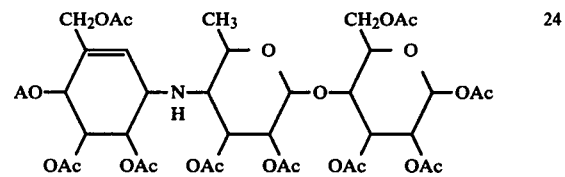

Hexadeca-O-acetyl-O-{4,6-dideoxy-4-[1S-(1,4,6/5)-4,5,6-trihydroxy-3-hydroxymethyl-4-O-α-D-glucopyranosyl-(1→4)-cyclohex-2-en-1-ylamino]-α-D-glucopyranosyl}-(1→4)-O-α-D-glcp-(1→4)-D-glucopyranose

EXAMPLE 9:

Dodeca-O-acetyl-O-{C}-(1→4)-O-α-D-glcp-(1→4)-α-D-glucopyranosyl bromide

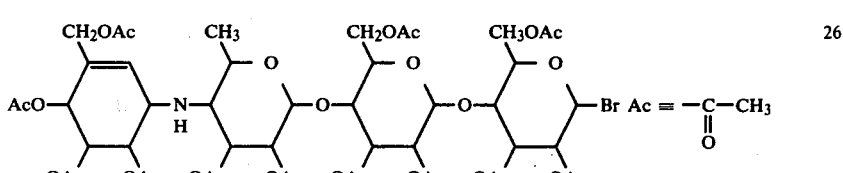

5 g of 23 were dissolved in 15 ml of glacial acetic acid. 10 ml of a saturated solution of hydrogen bromide in glacial acetic acid were added to the ice-cooled solution. The mixture was then stirred for 1 hour, whilst cooling with an ice bath. It was then diluted with chloroform and the chloroform solution was extracted by shaking with ice-water, until the wash water was neutral.

The chloroform solution was dried with Na₂SO₄, filtered and evaporated. Yield: 4.6 g of 26.

The non-crystalline crude product is used without further purification for the preparation of the glucoside.

The following compounds were prepared in an analogous way:

Nona-O-acetyl-O-{C}-(1→4)-α-D-glucopyranosyl bromide 27

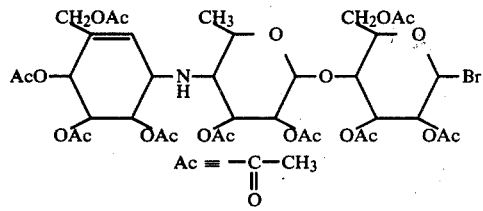

Ac = —C—CH₃
     ‖
     O

Pentadeca-O-acetyl-O-4,6-dideoxy-4-[IS-(1,4,6/5)-4,5,6-trihydroxy-3-hydroxymethyl-4-O-α-D-glucopyranosyl-(1→4)-cylohex-2-en-1-ylamino]-α-D-glucopyranosyl-(1→4)-O-α-D-glcp-(1→4)-α-D-glucopyranosyl bromide

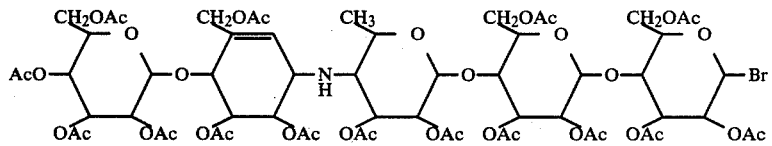

EXAMPLE 10:

Phenyl-O-{C}-(1→4)-O-α-D-glcp-(1→4)-β-D-thioglucopyranoside

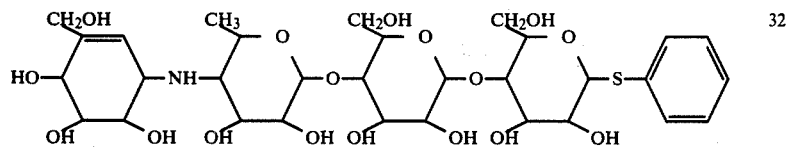

2.424 g of compound 26 from Example 9 is added to an ice-cold solution of 0.264 g (2 mmols) of sodium thiophenolate in 10 ml of absolute dimethylformamide and the mixture is stirred for 24 hours at room temperature, with the exclusion of moisture. It is concentrated to dryness in vacuo. The evaporation residue is taken up in chloroform/water, the phases are separated and the chloroform phase is washed 2× with water, dried and evaporated in vacuo. The resulting residue is stirred for 1 hour in an ice-bath with a solution of 100 mg of sodium in 25 ml of absolute methanol and the resulting suspension is rendered neutral with absolute glacial acetic acid and concentrated in a rotary evaporator. The residue is taken up in a little dimethylformamide/water/butanol and discharged onto a column (length: 65 cm; φ: 3 cm) filled with cellulose (Avicel, Merck). The column is eluted with butanol which is saturated with water and the individual fractions are examined by thin layer chromatography. 670 mg of the non-crystalline compound 32 with an optical rotation value $\alpha_D \times 106.7°$ (H₂O; C=1%) are obtained.

Molecular weight of the acetylated compound, determined by mass spectrometry: 1,241 (C₅₅H₇₁NO₂₉S).

The following compounds were prepared analogously:

2-Aminophenyl-O-{C}-(1→4)-O-α-D-glcp-(1→4)-β-D-thioglucopyranoside 33

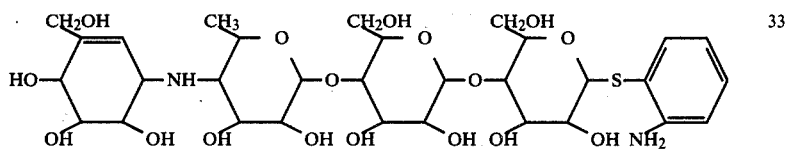

$\alpha_D$ 71.7° (H₂O; C=1%)
Molecular weight of the acetylated compound, determined by mass spectrometry: 1,298 (C₅₇H₇₄N₂O₃₀S).

2-Benzthiazolyl-O-{C}-(1→4)-O-α-D-glcp-(1→4)-β-D-thioglucopyranoside

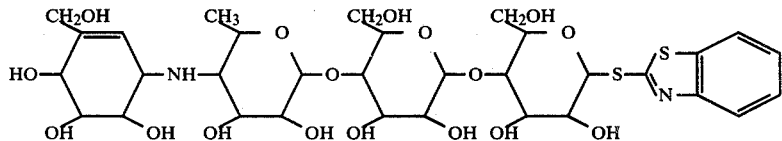

34:
$\alpha_D$ = 66.9° (H₂O; C=1%).

The mass spectrum of the acetylated compound was measured.

Benzyl-O-{C}-(1→4)-O-α-D-glcp-(1→4)-β-D-thio-
glucopyranoside

38:
Indolyl-3-O-{C∓-(1→4)-O-α-D-glcp-(1→4)-β-D-
glucopyranoside

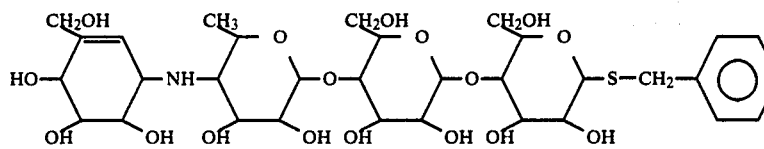

Molecular weight of the acetylated compound, determined by mass spectrometry: 1,255 ($C_{56}H_{73}NO_{29}S$).

36:

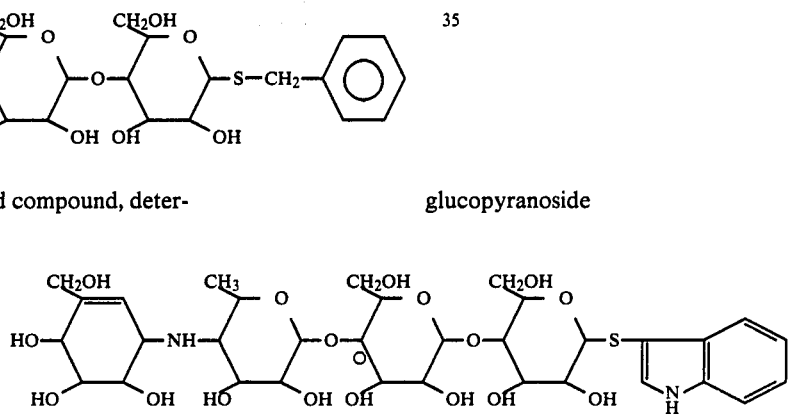

4-Carboxymethyl-phenyl-O-{C}-(1→4)-O-α-D-glcp-
(1→4)-β-D-thioglycopyranoside

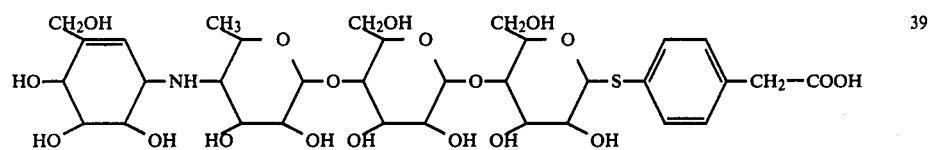

4-Phenoxy-phenyl-O-{C}-(1→4)-O-α-D-glcp-(1→4)-β-
D-thioglucopyranoside

Molecular weight of the acetylated compound, determined by mass spectrometry: 1,299 ($C_{57}H_{73}NO_{31}S$).

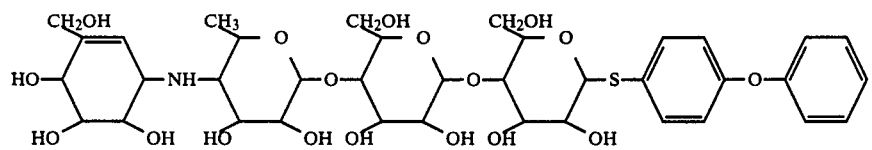

Molecular weight of the acetylated compound, determined by mass spectrometry: 1,333 ($C_{61}H_{75}NO_{30}S$) $_D107.5°$ (C=1; $H_2O$).

37:
4-Aminophenyl-O-{C}-(1→4)-O-α-D-glcp-(1→4)-β-D-
thioglucopyranoside $α_D = 101.3°$ ($H_2O$; C=1)

Pyridyl-4-O-{C}-(1→4)-O-α-D-glcp-(1→4)-D-
glucopyranoside

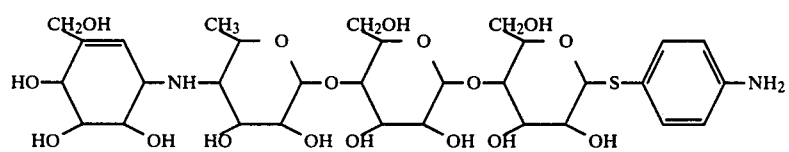

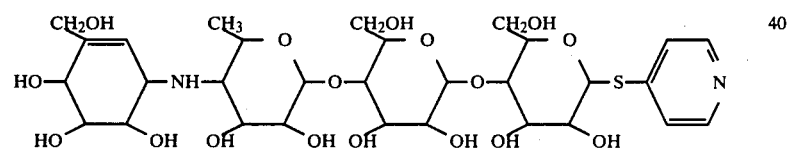

EXAMPLE 11:

N-p-Tolyl-O-{C}-(1→4)-O-α-D-glcp-(1→4)-D-glucopyranoslyamine

N-Phenyl-O-{C}-(1→4)-O-α-D-glcp-(1→4)-D-glucopyranosylamine

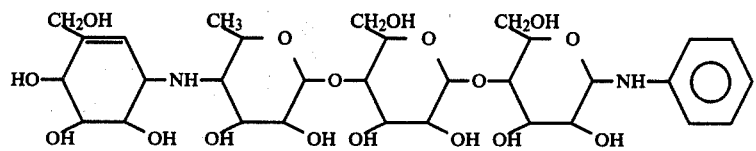

37

$\alpha_D = 97.6°$ (H$_2$O; C=1)

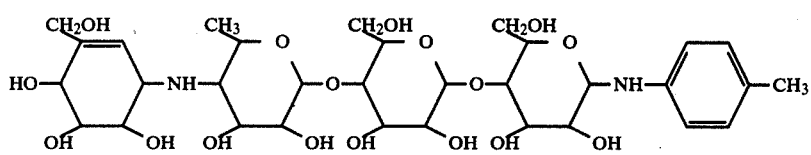

36

A solution of 1 g of p-toluidine in 4.8 ml of absolute ethanol is added to a solution of 1 g of compound I (m=0) n=2) in 2 ml of 0.001 N sulphuric acid. The mixture is stirred for 3 days at room temperature, 400 mg of barium carbonate are added, the mixture is filtered and the filtrate is concentrated in a rotary evaporator. The evaporation residue is dired in a desiccator, triturated with ether, filtered off and washed with ether. The resulting crude product (1.1 g) is dissolved in a little methanol and discharged onto a column (length: 70 cm; φ: 2.6 cm) filled with cellulose (Avicel, Merck). The column is eluted with a 4:1 methanol/ethanol mixture and the individual fractions are examined by thin layer chromatography.

330 mg of a non-crystalline compound with an optical rotation value $\alpha_D = 109.1°$ (H$_2$O; C=1%) are obtained.

The molecular weight of the acetyl compound, determined by mass spectrometry, is 1,238 (C$_{56}$H$_{74}$N$_2$O$_{29}$).

The following compounds were prepared analogously:

Molecular weight of the acetylated compound, determined by mass spectrometry: 1,224 (C$_{55}$H$_{72}$N$_2$O$_{29}$)

O-{C}-(1→4)-O-α-D-glcp-(1→4)-D-glucopyranosyl-morpholine

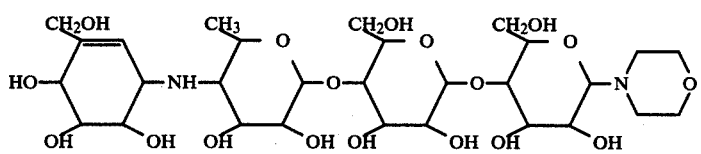

38

Molecular weight of the acetylated compound, determined by mass spectrometry: 1,218 (C$_{53}$H$_{74}$N$_2$O$_{30}$).

39:
O-{C}-(1→4)-O-α-D-glcp-(1→4)-D-glucopyranosyl-N'-phenylpiperazine

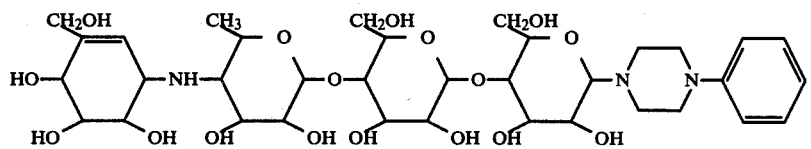

Molecular weight of the acetylated compound, determined by mass spectrometry: 1,293 (C$_{59}$H$_{79}$N$_3$O$_{29}$)
$\alpha_D = 127.1$ (H$_2$O; C=1)

40:
N-(p-Methoxy-phenyl)-O-{C}-(1→4)-O-α-D-glcp-(1→4)-D-glucopyranosylamine

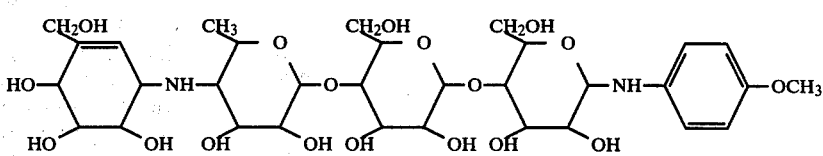

Molecular weight of the acetylated compound, determined by mass spectrometry: 1,254 (C$_{56}$H$_{74}$N$_2$O$_{30}$)
$\alpha_D = 133.5$ (H$_2$O; C=1)

41:
N-Benzyl-O-{C}-(1→4)-O-α-D-glcp-(1→4)-D-glucopyranosylamine

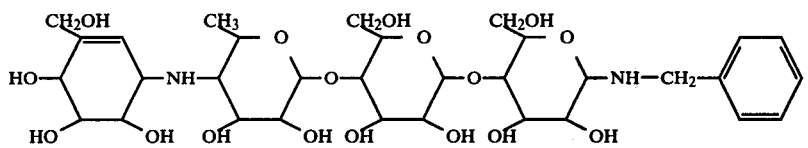

Molecular weight of the acetylated compound, determined by mass spectrometry: 1,280 (C$_{58}$H$_{76}$N$_2$O$_{30}$)
α$_D$=144.1 (H$_2$O; C=1)

42: N-(p-Acetylamino-phenyl)-O-{C}-(1→4)-O-α-D-glcp-(1→4)-D-glucopyranosylamine

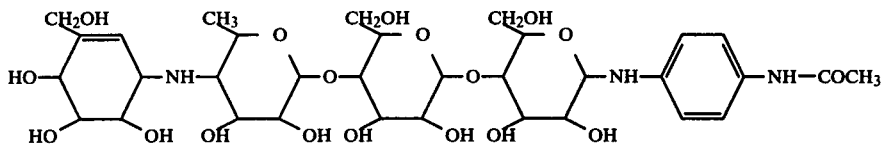

Molecular weight of the acetylated compound, determined by mass spectrometry: 1,281 (C$_{57}$H$_{75}$N$_3$O$_{30}$)
α$_D$=122.2 (H$_2$O; C=1)

EXAMPLE 12

O-{C}-(1→4)-O-α-D-glcp-(1→4)-1-thio-D-glucopyranose

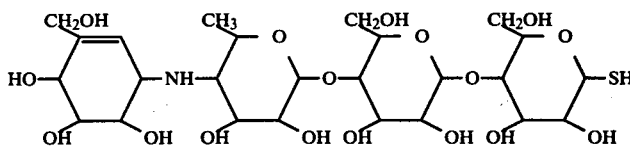

(A) 22.24 g (20 mmols) of compound 26 from Example 9 are added to a suspension of 1.56 g (20 mmols) of thiourea in 20 ml acetone and the mixture is stirred for 15 minutes under reflux, with the exclusion of moisture. It is concentrated to dryness in vacuo. The crude product is used for the further reaction.

(B) 25.76 g (20 mmols) of dodeca-O-C-(1-4)-β-D-glucopyranosyl-isothiuronium bromide and 30 ml of carbon tetrachloride are added to a solution, heated to 85° C., of 3.41 g (17.9 mmols) of sodium pyrosulphite in 20 ml of water and the mixture is stirred for 10 minutes at 85° C. After cooling, it is diluted with chloroform, the phases are separated and the chloroform phase is washed 2 times with ice-water, dried and concentrated in vacuo. The residue is taken up in a little chloroform and discharged onto a column (length: 90 cm; φ: 4 cm) filled with silica gel 60 (Merck). The column is eluted with chloroform/ethyl acetate 2:1 and the individual fractions are examined by thin layer chromatography. 10.6 g of a non-crystalline compound are obtained.

Empirical formula: C$_{49}$H$_{67}$NO$_{29}$S

Mass spectrum: m/e=1,131 (corresponds to M - H$_2$S)

Thin layer chromatography: finished silica gel 60 F 254 plates (Merck)

Running agent: chloroform/ethyl acetate 1:2

Rf$_{rel}$=0.854 (relative to compound 26 from Example 9, Rf=1.0)

For de-acetylation, the compound is stirred with a solution of 1 g of sodium in 250 ml of absolute methanol in an ice bath for 2 hours, 100 ml of water are added to the resulting suspension and the mixture is rendered neutral with a weakly acid ion exchanger, that is to say Amberlite IRC 50 (Serva) and filtered and the filtrate is evaporated in vacuo. The residue is dissolved in a little water and the solution is freeze-dried. 6 g of a non-crystalline compound with an optical rotation α$_D$= +125.0° (H$_2$O; C=1) are obtained.

What is claimed is:

1. An amino-sugar derivative of the formula

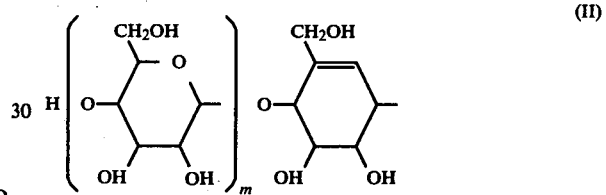

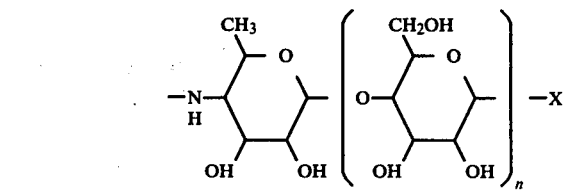

(II)

in which
n and m independently of each other represent an integer from 0 to 8 and the value of the sum n+m is an integer from 0 to 8 and
X represents a group —OR, —SH, —SR, —NH$_2$, —NHR or NRR$_1$, in which
R represents alkyl with 1 to 30 carbon atoms, alkenyl with 2 to 6 carbon atoms, cycloalkyl with 3 to 7 ring carbon atoms, aralkyl with 6 to 10 carbon atoms in the aryl part, monocyclic or bicyclic aryl with 6 to 10 carbon atoms, or heterocyclic with 5 to 6 ring members and 1 to 3 hetero-atoms, said alkyl being unsubstituted or substituted by up to 5 substituents, which substituents are hydroxyl; alkoxy with 1 to 4 carbon atoms; amino or monoalkylamino or dialkylamino with 1 to 4 carbon atoms per alkyl radical; mercapto or alkylthio with 1 to 4 carbon atoms; halogen; alkylcarbonyl with 1 to 4 carbon atoms in the alkyl radical; carboxyl; nitro; cyano; the aldehyde group and the sulphonic acid group, said alkenyl being unsubstituted or substituted by hydroxyl; alkoxy with 1 to 4 carbon atoms, mercapto, alkylthio with 1 to 4 carbon atoms, halogen or nitro, said cycloalkyl being unsubstituted or substituted with the substituents defined above where R is alkyl, said aryl and aralkyl being unsubstituted or substituted by up to 3 substituents, said substituents being alkyl having 1 to 10 carbon atoms which is, in turn, unsubstituted or substituted by chlorine, nitro or cyano; alkenyl with 1 to 10 carbon atoms, which is unsubstituted or substituted by cyano; cyclohexyl; hydroxyl or alkoxy with 1 to 4 carbon atoms; amino or monoalkylamino or dialkylamino with 1 to 4 carbon atoms per alkyl radical; mercapto or alkylthio with 1 to 4 carbon atoms; carboxyl or carboalkoxy with 1 to 4 carbon atoms; the sulphonic acid group; alkylsulphonyl with 1 to 4 carbon atoms; phenylsulphonyl; aminosulphonyl or alkylaminosulphonyl or dialkylaminosulphonyl with 1 to 4 carbon atoms per alkyl group; nitro, cyano; the aldehyde group; alkylcarbonylamino with 1 to 4 carbon atoms; alkylcarbonyl with 1 to 4 carbon atoms, benzoyl; benzylcarbonyl or phenylethylcarbonyl, each of said last-mentioned alkyl, phenyl, benzyl and phenylethyl groups being unsubstituted or, in turn, substituted by chloro, nitro or hydroxyl, said heterocyclic radical being unsubstituted or substituted by hydroxyl; amino; $C_1-C_4$-alkyl; benzene nuclei or further 6-membered heterocyclic rings fused to them with the bonding of the heterocyclic radical R in this case effected via a carbon atom of the heterocyclic system or of the fused benzene nucleus or where the bonding of the heterocyclic radical R is effected via a -$CH_2$-bridge outside the ring.

$R_1$ represents alkyl with 1 to 6 carbon atoms or cycloalkyl with 3 to 7 ring carbon atoms, aralkyl with 6 to 10 carbon atoms in the aryl part and 1 to 4 carbon atoms in the alkyl part, or monocyclic or bicyclic aryl with 6 to 10 carbon atoms, said radicals being unsubstituted or substituted by alkoxy with 1 to 4 carbon atoms; amino; $C_1-C_4$-monoalkylamino and $C_1-C_4$-dialkylamino; nitro; halogen; cyano; hydroxyl; mercapto; $C_1-C_4$-thioalkyl or the carboxyl or sulphonic acid group and, where $R_1$ denotes phenyl, also by $C_1-C_4$-alkyl, R and $R_1$, taken together with the nitrogen atom to which they are bonded, forms a 5 to 7 ring membered heterocyclic ring which is saturated or unsaturated and contains 0 to 3 additional oxygen atoms, sulphur atoms or nitrogen atoms, a $SO_2$ group or an N-alkyl group, in which the alkyl group contains 1 to 4 carbon atoms.

2. An amino-sugar derivative of claim 1 of the formula (II) in which

X represents a —OR, —SH, —SR, —$NH_2$, —NHR or $NRR_1$ group in which

R represents alkyl with 1 to 18 carbon atoms, which can be substituted by 1 to 5 hydroxyl or $C_1-C_4$ alkoxy groups, or represents phenyl which is optionally substituted by 1 to 3 $C_1-C_4$ alkyl, OH, $C_1-C_4$ alkoxy, amino, $C_1-C_4$ alkylamino, di-$C_1-C_4$ alkylamino, carboxyl, methoxycarbonyl, nitro, glucopyranyl, benzoyl, p-hydroxyphenylethylcarbonyl, $C_1-C_4$ alkylaminosulphonyl or $C_1-C_4$ dialkylaminosulphonyl or by a group

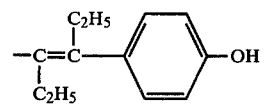

or represents benzyl or a 2-benzthiazolyl; and
$R_1$ designates $C_1-C_8$ alkyl or, together with R, forms a morpholine or piperidine ring.

3. An amino-sugar derivative of claim 1 of the formula

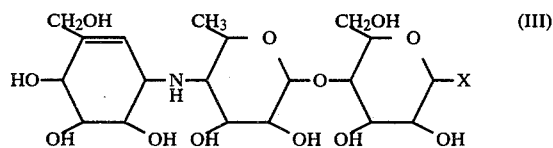

in which
X has the meaning given in claim 1.

4. An amino-sugar derivative of claim 1 of the formula

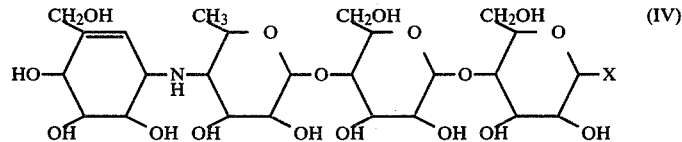

in which X has the meaning given in claim 1.

5. An amino-sugar derivative of claim 1 of the formula

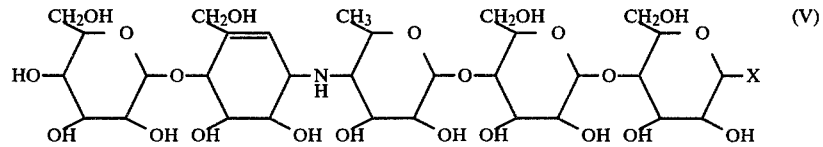

in which X has the meaning given in claim 1.

6. A pharmaceutical composition containing as an active ingredient an effective amount of a compound according to claim 1 in admixture with a solid or liquefied gaseous diluent.

7. A pharmaceutical composition containing as an active ingredient an effective amount of a compound according to claim 1 in the form of a sterile or isotonic aqueous solution.

8. A composition according to claim 6 containing from 0.5 to 95% by weight of the said active ingredient.

9. A medicament in dosage unit form comprising an effective amount of a compound according to claim 1 together with an inert pharmaceutical carrier.

10. A medicament of claim 9 in the form of tablets, pills, dragees, capsules, ampoules, or suppositories.

* * * * *

UNITED STATES PATENT AND TRADEMARK OFFICE
CERTIFICATE OF CORRECTION

PATENT NO. : 4,175,123
DATED : November 20, 1979
INVENTOR(S) : Bodo Junge, et al.

It is certified that error appears in the above-identified patent and that said Letters Patent are hereby corrected as shown below:

```
Column  1, line 12, "ae" should are --are--.
Column  1, line 68, "an" should be --a--.
Column 15, line 53, "OH" 1st occurr. should be --HO--.
Column 21, line 64, "30" 2nd occurr. should be --3--.
Column 23, line 37, "compound" should be --compounds--.
Column 25, line 63, "determine" should be --determined--.
Column 26, line 60, "weighted" should be --weighed--.
Column 29, Col. 5, line 11, Table III, "115 + 7.0"
  should be --115 $\pm$ 7.0--.
Column 48, line 2, delete "+" after "(" and insert
  --)--.
Column 49, line 38 "dired" should be --dried--.
```

Signed and Sealed this

*Eighteenth* Day of *March 1980*

[SEAL]

*Attest:*

SIDNEY A. DIAMOND

*Attesting Officer*     *Commissioner of Patents and Trademarks*